US008680116B2

(12) United States Patent
DeLeon et al.

(10) Patent No.: US 8,680,116 B2
(45) Date of Patent: Mar. 25, 2014

(54) QUINOLINONE PDE2 INHIBITORS

(75) Inventors: Pablo DeLeon, Philadelphia, PA (US);
Melissa Egbertson, Ambler, PA (US);
Ivory D. Hills, Harleysville, PA (US);
Adam Wayne Johnson, North Wales, PA (US); Michelle Machacek, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 159 days.

(21) Appl. No.: 13/384,946

(22) PCT Filed: Jul. 19, 2010

(86) PCT No.: PCT/US2010/042419
§ 371 (c)(1),
(2), (4) Date: Jan. 19, 2012

(87) PCT Pub. No.: WO2011/011312
PCT Pub. Date: Jan. 27, 2011

(65) Prior Publication Data
US 2012/0115885 A1 May 10, 2012

Related U.S. Application Data

(60) Provisional application No. 61/227,650, filed on Jul. 22, 2009, provisional application No. 61/298,602, filed on Jan. 27, 2010.

(51) Int. Cl.
*A61K 31/04* (2006.01)
*C07D 215/38* (2006.01)
(52) U.S. Cl.
USPC .......................................... 514/312; 546/159
(58) Field of Classification Search
USPC .......................................... 546/159; 514/312
See application file for complete search history.

(56) References Cited

U.S. PATENT DOCUMENTS

| 4,607,039 A * | 8/1986 | Le Count et al. ............. 514/312 |
| 6,150,522 A * | 11/2000 | Goulet et al. ................. 544/328 |
| 7,326,788 B2 * | 2/2008 | Wall et al. .................... 546/157 |
| 2007/0135457 A1 | 6/2007 | Beyer et al. | |

FOREIGN PATENT DOCUMENTS

| EP | 1097707 | 11/2000 |
| EP | 1097706 | 5/2005 |
| WO | WO9311115 | 6/1993 |
| WO | WO03066630 | 8/2003 |
| WO | WO2004058260 | 7/2004 |
| WO | WO2005000967 | 2/2005 |
| WO | WO2006032470 | 3/2006 |

OTHER PUBLICATIONS

Krayushkin, Russ J Org Chem, vol. 43, No. 9, pp. 1357-1363, 2007.*
Peifer, Bioorg & Med Chem Letters, vol. 18, pp. 1431-1435, 2008.*
Blackburn, J Med Chem, vol. 30, pp. 2252-2259, 1987.*
Lieberman et al., "Effectiveness of Antipsychotic Drugs in Patients with Chronic Schizophrenia", New England J. of Medicine, 2005, vol. 353, pp. 1209-1223, Massachusetts Medical Society.
Juilfs et al., "Cyclic GMP as Substrate and Regulator of Cyclic Nucleotide Phosphodiesterases (PDEs)", Rev. Physio. Biochem Pharm., 1999, vol. 135, pp. 67-104.
Van Staveren et al., "The effects of Phosphodiesterase Inhibition on Cyclic GMP and Cyclic AMP Accumulation in the Hippocampus of the Rat", Brain Research, 2001, vol. 888, pp. 275-286.
Suvarna et al., Hydrolysis of N-Methyl-d-Aspartate Receptor-Stimulated cAMP and cGMP by PDE4 and PDE2 Phosphodiesterases in Primary Neuronal Cultures of Rat Cerebral Cortex and Hippocampus, JPET, 2002, vol. 302, pp. 249-256, The American Society for Pharmacology and Experimental Therapeutics.
Velardez et al, "Role of Phosphodiesterase and Protein Kinase G on Nitric Oxide-Induced Inhibition of Prolactin Release from the Rat Anterior Pituitary", E. Journal of Endocrinology.
Cote et al., "Comparative Involvement of Cyclic Nucleotide Phosphodiesterases and Adenylyl Cyclase on Adrenocorticotropin-Induced Increase of Cyclic Adenosine Monophosphate in rat and Human Glomerulosa Cells", Endo., 1999,vol. 140, pp. 3594-3601, The Endocrine Society.
Ahlstrom et al., "Inactivation of Atrial Natriuretic Factor-Stimulated Cyclic Guanosine 3', 5'-Monophosphate (cGMP) in UMR-106, Osteoblast-Like Cells", Biochemical Pharmacology, 2000, vol. 59, pp. 1133-1139, Elsvier Science. Inc.
Wakabayashi et al., "Involvement of Phosphodiesterase Isozymes in Osteoblastic Differentiation",J. of Bone and Mineral Research, 2002, vol. 17, pp. 249-256, American Society for Bone and Mineral Research.
Michie et al., "Rapid Regulation of PDE-2 and PDE-4 Cyclic AMP Phosphodiesterase Activity Following Ligation of the T Cell Antigen Receptor on Thymocytes: Analysis Using the Selective Inhibitors Erythro-8-(2-Hydroxy-3-Nonyl)-Adenine (EHNA) and Rolipram", Cell Signal, 1996, vol. 8, pp. 97-110, Elsevier Science, Inc.
Kervais et al., "Cyclic Nucleotide Hydrolysis in Bovine Aortic Endothelial Cells in Culture: Differential Regulation in Cobblestone and Spindle Phenotypes", J. Vasc. Res, 2000, vol. 37, pp. 235-249, Karger AG, France.
Sadhu et al., "Differential Expression of the Cyclic GMP-Stimulated Phosphodiesterase PDE2A in Human Venous and Capillary Endothelial Cells", J. of Histochemistry & Cytochemistry, 1999, vol. 47, pp. 895-905, The Histochemical Society, Inc.
Rivet-Bastide et al., "cGMP-Stimulated Cyclic Nucleotide Phosphodiesterase Regulates the Basal Calcium Current in Human Atrial Myocytes", J. Clin. Invest, 1997, vol. 99, pp. 2710-2718, The American Society for Clinical Investigation, Inc.

(Continued)

*Primary Examiner* — D M Seaman
(74) *Attorney, Agent, or Firm* — Sylvia A. Ayler; John C. Todaro

(57) ABSTRACT

The present invention is directed to quinolinone compounds which are useful as therapeutic agents for the treatment of central nervous system disorders associated with phosphodiesterase 2 (PDE2). The present invention also relates to the use of such compounds for treating neurological and psychiatric disorders, such as schizophrenia, psychosis or Huntington's disease, and those associated with striatal hypofunction or basal ganglia dysfunction.

20 Claims, No Drawings

(56) References Cited

OTHER PUBLICATIONS

Donzeau-Gouge et al., "Cyclic GMP Regulation of the L-Type Ca2+ Channel Current in Human Atrial Myocytes", J. of Physiology, 2001, vol. 533, pp. 329-340.

Herring et al., "NO-cGMP Pathway increases the Hyperpolarisation-Activated Current, If, and Heart Rate During Adrengeric Stimulation", Cardiovascular Research, 2001, vol. 52, pp. 446-453, Elsevier Science B.V.

Dickinson et al., "Activation of cGMP-Stimulated Phosphodiesterase by Nitroprusside Limits cAMP Accumulation in Human Platelets: Effects on Platelet Aggregation", Biochem, 1997, vol. 323, pp. 371-377, Printed in Great Britain.

Haynes et al., "Erythro-9-(2-Hydroxy-3-Nonyl)Adenine Inhibits Cyclic-3,5-Guanosine Monophosphate-Stimulated Phosphodiesterase to Reverse Hypoxic Pulmonary Vasoconstriction in the Perfused Rat Lung", 1996, vol. 276, pp. 752-757, The American Society for Pharmacology and Experimental Therapeutics.

Huang et al., "A Fluorescence Polarization Assay for Cyclic Nucleotide Phosphodiesterases", 2002, vol. 7, pp. 215-222, Sage Social Science Collections.

Mosser et al., "Automation of In Vitro Dose-Inhibition Assays Utilizing the Tecan Genesis and an Integrated Software Package to Support the Drug Discovery Process", JALA, 2003, vol. 8, pp. 54-63, Merck Research Labs.

Foucaud et al., Structural Model of the N-Methyl-D-Aspartale Receptor Glycine Site Probed by Site-Directed Chemical Coupling, J. Biological Chemistry, 29003, vol. 278, pp. 24011-24017.

Peifer et al., Implications for Selectivity of 3,4-Diarylquinolinones as P38aMAP Kinase Inhibitors, Bioorganic & Medicinal Chemistry letters, 2008, vol. 18, pp. 1431-1435.

Zhong et al., "Design and Synthesis of Quinolin-2(1H)-One Derivatives as Potent CDK5 Inhibitors", Bioorganic & Medicinal Chemistry Letters. vol. 17, No. 19, Sep. 2007, Elsevier Science, GB.

Hewawasam et al., "The Synthesis and Structure-Activity Relationships of 4-Aryl-3-Aminoquinolin-2-Ones: A New Class of calcium Dependent, Large Conductance, Potassium (Maxi-K) Channel Openers Targeted for Post Stroke Neuroprotection", Bioorganic & Medicinal Chemistry Letters, vol. 12, pp. 1779-1783, 2002.

\* cited by examiner

QUINOLINONE PDE2 INHIBITORS

CROSS-REFERENCE TO RELATED APPLICATIONS

This application is the National Stage of International Application No. PCT/US2010/042419 filed on Jul. 19, 2010, which claims the benefit under 35 U.S.C. 119(e) of U.S. Provisional Application Nos. 61/227,650, filed Jul. 22, 2009 and 61/298,602 filed Jan. 27, 2010.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncomplicance or discontinuation of medication. Dissatisfaction with therapy is attributed to lack of efficacy or intolerable and unacceptable side affects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophasphate (cGMP) levels and the dopaminergic D2 receptor associated with cyclic adenosine monophosphate (cAMP). These ubiquitous second messengers are responsible for altering the function of many intracellular proteins. Cyclic AMP is thought to regulate the activity of cAMP-dependent protein kinase (PKA), which in turns phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these enzymes, known as 3',5'-cyclic nucleotide specific phosphodiesterases (PDEs). The PDE superfamily includes twenty one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45% suggests that it may be possible to develop selective inhibitors for each of these subtypes.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et. al., Brain Res., 888, 275 (2001) and J. O'Donnell, et. al., J. Pharm. Exp. Ther., 302, 249 (2002)); prolactin and aldosterone secretion (M. O. Velardez, et. al., Eur. J. Endo., 143, 279 (2000) and N. Gallo-Payet, et. al., Endo., 140, 3594 (1999)); bone cell differentiation, growth, and bone resorption (C. Allardt-Lamberg, et. al., Biochem. Pharm., 59, 1133 (2000) and S. Wakabayashi, et. al., J. Bone, Miner. Res., 17, 249 (2002); immunological response (M. D. Houslay, et. al., Cell. Signal., 8, 97 (1996); vascular angiogenesis (T. Keravis, et. al., J. Vasc. Res., 37, 235 (2000); inflammatory cell transit (S. L. Wolda, et. al., J. Histochem. Cytochem., 47, 895 (1999); cardiac contraction (R. Fischmeister, et. al., J. Clin. Invest., 99, 2710 (1997), P. Donzeau-Gouge, et al., J. Physiol., 533, 329 (2001), and D. J. Paterson, et. Al., Card. Res., 52, 446 (2001); platelet aggregation (R. J. Haslam, et. Al., Biochem. J., 323, 371 (1997); female sexual arousal discorder (C. P. Wayman, et. al., EP Patent Publications EP10977707 and EP1097706; and hypoxic pulmonary vasoconstriction (J. Haynes, et. al., J. Pharm. Exp. Ther., 276, 752 (1996). See also US2007135457, Inhibition of PDE2 is further believed to be useful in the treatment of schizophrenia as well as a wide variety of conditions or disorders that would benefit from increasing levels of cAMP and/or cGMP within neurons, including a variety neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to quinolinone compounds which are useful as therapeutic agents for the treatment of central nervous system disorders associated with phosphodiesterase 2 (PDE2). The present invention also relates to the use of such compounds for treating neurological and psychiatric disorders, such as schizophrenia, psychosis or Huntington's disease, and those associated with striatal hypofunction or basal ganglia dysfunction.

DETAILED DESCRIPTION OF THE INVENTION

The present invention is directed to compounds of the formula I:

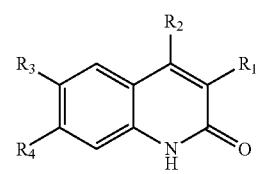

wherein:

$R_1$ is selected from the group consisting of:
(1) —$C_{5-6}$ heterocycle, which is unsubstituted or substituted with $R_{14}$;
(2) phenyl, which is unsubstituted or substituted with $R_{14}$;
(3) —$C_{1-6}$alkyl, which is unsubstituted or substituted with $R_{14}$;

$R_2$ is selected from the group consisting of
(1) —O($C_{1-6}$ alkyl), unsubstituted or substituted with $R_{14}$;
(2) —O($CH_2$)$_n$$C_{6-10}$aryl, which is unsubstituted or substituted with $R_{14}$;
(3) —O($CH_2$)$_n$$C_{3-10}$ cycloakyl;

(4) —O(CH$_2$)$_n$C$_{5-10}$ heterocycle, which is unsubstituted or substituted with R$_{14}$;
(5) phenyl, which is unsubstituted or substituted with R$_{14}$;
(6) —(CH$_2$)$_n$C$_{5-10}$heterocycle, which is unsubstituted or substituted with R$_{14}$;
(7) —(CH$_2$)$_n$C$_{5-10}$ aryl, which is unsubstituted or substituted with R$_{14}$;
(8) —(CH$_2$)$_n$C$_{3-10}$cycloakyl;
(9) —(C$_{2-6}$ alkenyl)C$_{5-10}$heterocycle, which is unsubstituted or substituted with R$_{14}$;
(10) —(C$_{2-6}$ alkenyl)C$_{6-10}$aryl, which is unsubstituted or substituted with R$_{14}$;
(11) —(C$_{2-6}$ alkenyl)C$_{3-10}$cycloalkyl, which is unsubstituted or substituted with R$_{14}$;

R$_3$ is selected from the group consisting of:
(1) Hydrogen
(2) Halogen
(3) —C$_{6-10}$aryl, which is unsubstituted or substituted with R$_{14}$;
(4) —C$_{5-10}$heteroaryl, which is unsubstituted or substituted with R$_{14}$;
(5) -(Q)C$_{6-10}$aryl, which is unsubstituted or substituted with R$_{14}$;
(6) -(Q)C$_{5-10}$heteroaryl, which is unsubstituted or substituted with R$_{14}$;
(7) -(Q)-C(R$_5$,R$_6$)—OH;
(8) —CN;
(9) —C$_{2-4}$ alkenyl;
(10) —OC$_{1-6}$ alkyl;

Q is selected independently from:
(1) —C$_{1-6}$ alkyl;
(2) —C$_{2-4}$ alkynyl;
(3) —C$_{2-4}$ alkenyl;

R$_4$, is selected independently from
(1) Hydrogen;
(2) —(CH$_2$)$_n$CH$_3$;
(3) —OC$_{1-6}$ alkyl;
(4) Halogen R$_5$ and R$_6$ are selected independently from
(1) Hydrogen;
(2) —(CH$_2$)$_n$CH$_3$,
(3) —OC$_{1-6}$ alkyl;

R$_{14}$ is selected from the group consisting of
(1) Hydroxyl;
(2) Halogen;
(3) C$_{1-6}$alkyl;
(4) —CN;
(5) —CO$_2$H;
(6) —C(O)NH$_2$;
(7) —(CH$_2$)$_n$C$_{6-10}$aryl;
(8) —(CH$_2$)$_n$C$_{5-10}$heterocycle;
(9) —NO$_2$;
(10) -(Q)-C(R$_5$,R$_6$)—OH;
(11) -Q(CH$_2$)$_n$C$_{5-10}$heteroaryl, which is unsubstituted or substituted with R$_{15}$;
(12) —(CH$_2$)$_n$C$_{3-10}$cycloakyl;
(13) -Q(CH$_2$)$_n$C$_{6-10}$aryl, which is unsubstituted or substituted with R$_{15}$;

R$^{15}$ is selected from the group consisting of:
(1) Hydroxyl;
(2) Halogen;
(3) C$_{1-6}$alkyl;
(4) —CN; and n is 0-3;
or a pharmaceutically acceptable salt thereof.

An embodiment of the present invention is realized when R$_1$ is C$_{5-6}$ heterocycle, which is unsubstituted or substituted with R$_{14}$, and all other variables are as originally described. A sub-embodiment of this invention is realized when the heterocycle is thiophenyl or pyridyl. Another sub-embodiment of this invention is realized when the heterocycle is thiophenyl. Another sub-embodiment of this invention is realized when the heterocycle is pyridyl. Another sub-embodiment of this invention is realized when the heterocycle is unsubstituted. Still another sub-embodiment of this invention is realized when the heterocycle is substituted.

Another embodiment of the present invention is realized when R$_1$ is phenyl, which is unsubstituted or substituted with R$_{14}$, and all other variables are as originally described. Another sub-embodiment of this invention is realized when the phenyl is unsubstituted. Still another sub-embodiment of this invention is realized when the phenyl is substituted.

Another embodiment of the present invention is realized when R$_1$ is C$_{1-6}$alkyl, which is unsubstituted or substituted with R$_{14}$, and all other variables are as originally described. A subembodiment of this invention is realized when said alkyl is selected from the group consisting of methyl, ethyl, propyl, and isopropyl. Another sub-embodiment of this invention is realized when the alkyl is unsubstituted. Still another sub-embodiment of this invention is realized when the alkyl is substituted.

Another embodiment of the present invention is realized when R$_2$ is —O(alkyl), unsubstituted or substituted with R$_{14}$, and all other variables are as originally described.

Another embodiment of the present invention is realized when R$_2$ is —O(CH$_2$)$_n$C$_{6-10}$aryl, unsubstituted or substituted with R$_{14}$, and all other variables are as originally described. A subembodiment of this invention is realized when said aryl is phenyl and n is 0-1.

Another embodiment of the present invention is realized when R$_2$ is —O(CH$_4$C$_{3-10}$cycloakyl, unsubstituted or substituted with R$_{14}$, and all other variables are as originally described. A subembodiment of this invention is realized when said cycloalkyl is cyclohexyl and n is 0-1.

Another embodiment of the present invention is realized when R$_2$ is —O(CH$_2$)$_n$C$_{5-10}$heterocycle, unsubstituted or substituted with R$_{14}$, and all other variables are as originally described. A subembodiment of this invention is realized when said heterocycle is selected from the group consisting of pyranyl, pyridyl and piperidinyl and n is 0-1.

Another embodiment of the present invention is realized when R$_2$ is phenyl, unsubstituted or substituted with R$_{14}$, and all other variables are as originally described.

Another embodiment of the present invention is realized when R$_2$ is —(C$_2$H$_2$)$_n$C$_{5-10}$heterocycle, unsubstituted or substituted with R$_{14}$, and all other variables are as originally described. A subembodiment of this invention is realized when said heterocycle is selected from the group consisting of pyranyl, pyridyl and piperidinyl and n is 0-1.

Another embodiment of the present invention is realized when R$_2$ is —(C$_2$H$_2$)$_n$C$_{6-10}$aryl, unsubstituted or substituted with R$_{14}$, and all other variables are as originally described. A subembodiment of this invention is realized when said aryl is phenyl and n is 0-1.

Another embodiment of the present invention is realized when R$_2$ is —(C$_2$H$_2$)$_n$cycloakyl, unsubstituted or substituted with R$_{14}$, and all other variables are as originally described. A subembodiment of this invention is realized when said cycloalkyl is cyclohexyl and n is 0-1.

Another embodiment of the present invention is realized when R$_2$ is —(C$_{2-6}$ alkenyl)C$_{5-10}$heterocycle, unsubstituted or substituted with R$_{14}$, and all other variables are as originally described. A subembodiment of this invention is realized when said heterocycle is selected from the group consisting of pyranyl, pyridyl and piperidinyl and said alkenyl is ethylene.

Another embodiment of the present invention is realized when R$_3$ is hydrogen and all other variables are as originally described.

Another embodiment of the present invention is realized when $R_4$ is hydrogen and all other variables are as originally described.

Another embodiment of the present invention is realized when $R_3$ and $R_4$ both are hydrogen and all other variables are as originally described.

Another embodiment of the present invention is realized when $R_3$ and $R_4$ both are $C_{1-4}$ alkoxy, preferably methoxy and all other variables are as originally described.

Another embodiment of the present invention is realized when $R_3$ is not hydrogen and $R_4$ is hydrogen and all other variables are as originally described.

Another embodiment of the present invention is realized when $R_3$ is halogen and all other variables are as originally described. A subembodiment of this invention is realized when said halogen is bromine, or iodide, preferably bromine.

Another embodiment of the present invention is realized when $R_3$ is —$C_{6-10}$aryl, which is unsubstituted or substituted with $R_{14}$, and all other variables are as originally described. A subembodiment of this invention is realized when the aryl is phenyl.

Another embodiment of the present invention is realized when $R_3$ is —$C_{5-10}$heteroaryl, which is unsubstituted or substituted with $R_{14}$, and all other variables are as originally described. A subembodiment of this invention is realized when the heteroaryl is pyridyl, pyrazolyl, or pyrimidinyl.

Another embodiment of the present invention is realized when $R_3$ is -(Q)$C_{6-10}$aryl, which is unsubstituted or substituted with $R_{14}$, and all other variables are as originally described. A subembodiment of this invention is realized when the aryl in -(Q)$C_{6-10}$aryl is phenyl and the Q is $C_2$alkynyl.

Another embodiment of the present invention is realized when $R_3$ is -(Q)$C_{5-10}$heteroaryl, which is unsubstituted or substituted with $R_{14}$ and all other variables are as originally described. A subembodiment of this invention is realized when the heteroaryl is pyridyl, pyrazolyl, or pyrimidinyl, and the Q is $C_2$alkynyl.

Another embodiment of the present invention is realized when $R_3$ is -(Q)-C($R_5,R_6$)—OH, which is unsubstituted or substituted with $R_{14}$ and all other variables are as originally described. A subembodiment of this invention is realized when $R_5$ and $R_6$ are both $C_{1-6}$ alkyl and the Q is $C_2$alkynyl.

Another embodiment of the present invention is realized when $R_3$ is —CN, which is unsubstituted or substituted with $R_{14}$ and all other variables are as originally described.

Another embodiment of the present invention is realized when $R_3$ is $C_{2-4}$ alkenyl, which is unsubstituted or substituted with $R_{14}$ and all other variables are as originally described.

An embodiment of the present invention includes compounds of the formula Ia:

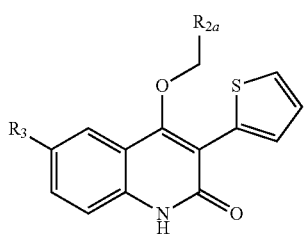

Ia wherein $R_3$ is defined herein and $R_{2a}$ is selected from the group consisting of $C_{1-6}$ alkyl, $C_{6-10}$ aryl, —$C_{3-10}$ cycloakyl, and $C_{5-10}$ heterocycle, said alkyl, aryl, heterocycle unsubstituted or substituted with $R_{14}$; or a pharmaceutically acceptable salt thereof. A subembodiment of this invention is realized when $R_{2a}$ is selected from the group consisting of pyranyl, pyridyl, piperidinyl, phenyl, and cyclohexyl. Still another embodiment of this invention is realized when $R_{2a}$ is selected from the group consisting of pyranyl, and pyridyl. Yet another embodiment of this invention is realized when $R_3$ is selected from the group consisting of hydrogen, halogen, -(Q)-C($R_5,R_6$)—OH, -(Q)$C_{6-10}$aryl and -(Q)$C_{5-10}$ heterocycle, said aryl and heterocycle unsubstituted or substituted with 1 to 3 of $R_{14}$, $R_5$ and $R_6$ are $C_{1-6}$ alkyl, and Q is $C_2$alkynyl. A further subembodiment of $R_3$ is realized when $R_5$ and $R_6$ are methyl, aryl is phenyl, and heterocycle is selected from the group consisting of pyridyl, pyrazolyl, or pyrimidinyl. Still another subembodiment of this invention is realized when $R_2$ is pyranyl, or pyridyl, substituted or unsubstituted, and $R_3$ is hydrogen, bromine, iodide, or —C≡C—C(CH$_3$)$_2$OH.

An embodiment of the present invention includes compounds of the formula Ib:

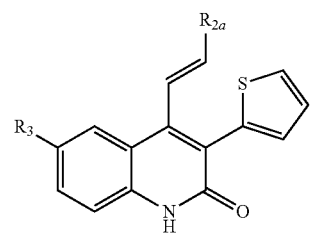

Ib wherein $R_3$ is defined herein and $R_{ea}$ is selected from the group consisting of $C_{6-10}$ aryl, —$C_{3-10}$ cycloakyl, and $C_{5-10}$ heterocycle, said aryl, heterocycle unsubstituted or substituted with $R_{14}$, or a pharmaceutically acceptable salt thereof. A subembodiment of this invention is realized when $R_{2a}$ is selected from the group consisting of pyranyl, pyridyl, piperidinyl, phenyl, and cyclohexyl. Still another embodiment of this invention is realized when $R_{2a}$ is selected from the group consisting of pyranyl, and pyridyl. Yet another embodiment of this invention is realized when $R_3$ is selected from the group consisting of hydrogen, halogen, -(Q)-C($R_5,R_6$)—OH, -(Q)$C_{6-10}$aryl and -(Q)$C_{5-10}$ heterocycle, said aryl and heterocycle unsubstituted or substituted with 1 to 3 of $R_{14}$, $R_5$ and $R_6$ are $C_{1-6}$ alkyl, and Q is $C_2$alkynyl. A further subembodiment of $R_3$ is realized when $R_5$ and $R_6$ are methyl, aryl is phenyl, and heterocycle is selected from the group consisting of pyridyl, pyrazolyl, or pyrimidinyl. Still another subembodiment of this invention is realized when $R_2$ is pyranyl, or pyridyl, substituted or unsubstituted, and $R_3$ is hydrogen, bromine, iodide, or —C≡C—C(CH$_3$)$_2$OH.

An embodiment of the present invention includes compounds of the formula Ic:

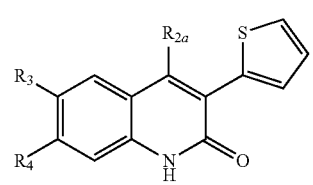

Ic wherein $R_3$ and $R_4$ are defined herein and $R_{2a}$ is selected from the group consisting of $C_{6-10}$ aryl, —$C_{3-10}$ cycloakyl, and $C_{5-10}$ heterocycle, said aryl, heterocycle unsubstituted or substituted with $R_{14}$, or a pharmaceutically acceptable salt thereof. A subembodiment of this invention is realized when $R_{2a}$ is selected from the group consisting of pyranyl, pyridyl, piperidinyl, phenyl, and cyclohexyl. Still another embodiment of this invention is realized when $R_{2a}$ is selected from the group consisting of pyranyl, phenyl and pyridyl. Yet another embodiment of this invention is realized when $R_3$ is selected from the group consisting of hydrogen, halogen, -(Q)-C($R_5$,$R_6$)—OH, -(Q)$C_{6-10}$aryl and -(Q)$C_{5-10}$ heterocycle, said aryl and heterocycle unsubstituted or substituted with 1 to 3 of $R_{14}$, $R_5$ and $R_6$ are $C_{1-6}$ alkyl, and Q is $C_2$alkynyl. A further subembodiment of $R_3$ is realized when $R_5$ and $R_6$ are methyl, aryl is phenyl, and heterocycle is selected from the group consisting of pyridyl, pyrazolyl, or pyrimidinyl. Still another subembodiment of this invention is realized when $R_2$ is pyranyl, phenyl, or pyridyl, substituted or unsubstituted, and $R_3$ is hydrogen, bromine, iodide, or —C≡C—C(CH$_3$)$_2$OH.

An embodiment of the present invention includes compounds of the formula Id:

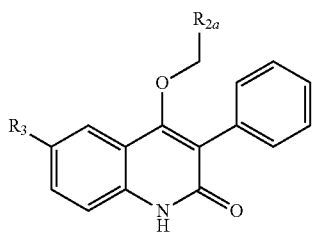

Id wherein $R_3$ is defined herein and $R_{2a}$ is selected from the group consisting of $C_{1-6}$ alkyl, $C_{6-10}$ aryl, —$C_{3-10}$ cycloakyl, and $C_{5-10}$ heterocycle, said alkyl, aryl, heterocycle unsubstituted or substituted with $R_{14}$; or a pharmaceutically acceptable salt thereof. A subembodiment of this invention is realized when $R_{2a}$ is selected from the group consisting of pyranyl, pyridyl, piperidinyl, phenyl, and cyclohexyl. Still another embodiment of this invention is realized when $R_{2a}$ is selected from the group consisting of pyranyl, and pyridyl. Yet another embodiment of this invention is realized when $R_3$ is selected from the group consisting of hydrogen, halogen, -(Q)-C($R_5$,$R_6$)—OH, -(Q)$C_{6-10}$aryl and -(Q)$C_{5-10}$ heterocycle, said aryl and heterocycle unsubstituted or substituted with 1 to 3 of $R_{14}$, $R_5$ and $R_6$ are $C_{1-6}$ alkyl, and Q is $C_2$alkynyl. A further subembodiment of $R_3$ is realized when $R_5$ and $R_6$ are methyl, aryl is phenyl, and heterocycle is selected from the group consisting of pyridyl, pyrazolyl, or pyrimidinyl. Still another subembodiment of this invention is realized when $R_2$ is pyranyl, or pyridyl, substituted or unsubstituted, and $R_3$ is s hydrogen, bromine, iodide, or —C≡C—C(CH$_3$)$_2$OH.

An embodiment of the present invention includes compounds of the formula Ie:

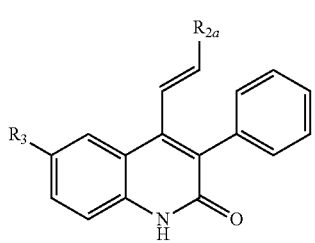

Ie wherein $R_3$ is defined herein and $R_{2a}$ is selected from the group consisting of $C_{6-10}$ aryl, —$C_{3-10}$ cycloakyl, and $C_{5-10}$ heterocycle, said aryl, heterocycle unsubstituted or substituted with $R_{14}$, or a pharmaceutically acceptable salt thereof. A subembodiment of this invention is realized when $R_{2a}$ is selected from the group consisting of pyranyl, pyridyl, piperidinyl, phenyl, and cyclohexyl. Still another embodiment of this invention is realized when $R_{2a}$ is selected from the group consisting of pyranyl, and pyridyl. Yet another embodiment of this invention is realized when $R_3$ is selected from the group consisting of hydrogen, halogen, -(Q)-C($R_5$,$R_6$)—OH, -(Q)$C_{6-10}$aryl and -(Q)$C_{5-10}$ heterocycle, said aryl and heterocycle unsubstituted or substituted with 1 to 3 of $R_{14}$, $R_5$ and $R_6$ are $C_{1-6}$ alkyl, and Q is $C_2$alkynyl. A further subembodiment of $R_3$ is realized when $R_5$ and $R_6$ are methyl, aryl is phenyl, and heterocycle is selected from the group consisting of pyridyl, pyrazolyl, or pyrimidinyl. Still another subembodiment of this invention is realized when $R_2$ is pyranyl, or pyridyl, substituted or unsubstituted, and $R_3$ is hydrogen, bromine, iodide, or —C≡C—C(CH$_3$)$_2$OH.

An embodiment of the present invention includes compounds of the formula If:

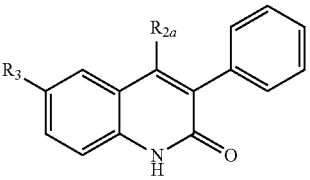

If wherein $R_3$ is defined herein and $R_{2a}$ is selected from the group consisting of $C_{6-10}$ aryl, —$C_{3-10}$ cycloakyl, and $C_{5-10}$ heterocycle, said aryl, heterocycle unsubstituted or substituted with $R_{14}$, or a pharmaceutically acceptable salt thereof. A subembodiment of this invention is realized when $R_{2a}$ is selected from the group consisting of pyranyl, pyridyl, piperidinyl, phenyl, and cyclohexyl. Still another embodiment of this invention is realized when $R_{2a}$ is selected from the group consisting of pyranyl, phenyl and pyridyl. Yet another embodiment of this invention is realized when $R_3$ is selected from the group consisting of hydrogen, halogen, -(Q)-C($R_5$, $R_6$)—OH, -(Q)$C_{6-10}$aryl and -(Q)$C_{5-10}$ heterocycle, said aryl and heterocycle unsubstituted or substituted with 1 to 3 of $R_{14}$, $R_5$ and $R_6$ are $C_{1-6}$ alkyl, and Q is $C_2$alkynyl. A further subembodiment of $R_3$ is realized when $R_5$ and $R_6$ are methyl, aryl is phenyl, and heterocycle is selected from the group consisting of pyridyl, pyrazolyl, or pyrimidinyl. Still another subembodiment of this invention is realized when $R_2$ is pyranyl, phenyl, or pyridyl, substituted or unsubstituted, and $R_3$ is hydrogen, bromine, iodide, or —C≡C—C(CH$_3$)$_2$OH.

An embodiment of the present invention includes compounds of the formula Ig:

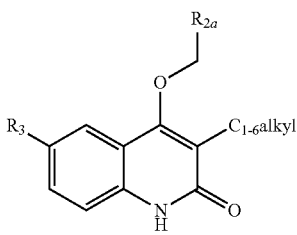

wherein $R_3$ and $R_{2a}$ are defined herein; or a pharmaceutically acceptable salt thereof.

An embodiment of the present invention includes compounds of the formula Ih:

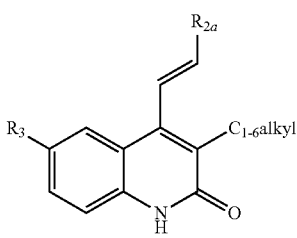

wherein $R_3$ and $R_{2a}$ are defined herein; or a pharmaceutically acceptable salt thereof.

An embodiment of the present invention includes compounds of the formula Ii:

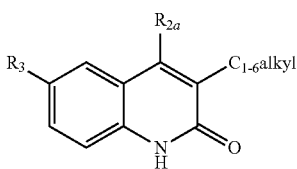

wherein $R_3$ and $R_{2a}$ are defined herein; or a pharmaceutically acceptable salt thereof.

Examples of compounds of this invention are found in Table 1 of the following pages. Specific embodiments of the present invention include a compound which is selected from the group consisting of the subject compounds of the Examples herein and pharmaceutically acceptable salts thereof and individual enantiomers and diastereomers thereof.

When any variable (e.g. aryl, heterocycle, $R^1$, $R^5$ etc.) occurs more than one time in any constituent, its definition on each occurrence is independent at every other occurrence. A group which is designated as being substituted with substituents may be substituted with multiple numbers of such substituents. A group which is designated as being independently substituted with substituents may be independently substituted with multiple numbers of such substituents. Also, combinations of substituents/or variables are permissible only if such combinations result in stable compounds.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

As appreciated by those of skill in the art, halogen or halo as used herein are intended to include fluorine, chlorine, bromine and iodine. Similarly, "alkyl", as well as other groups having the prefix "alk", such as alkoxy, alkanoyl, means carbon chains which may be linear or branched or combinations thereof. $C_{1-6}$, as in $C_{1-6}$alkyl is defined to identify the group as having 1, 2, 3, 4, 5 or 6 carbons in a linear or branched arrangement, such as methyl, ethyl, n-propyl, isopropyl, n-butyl, iso-butyl, sec-butyl, tert-butyl, pentyl, hexyl, and the like. "Alkylene" means a straight or branched chain of carbon atoms with a group substituted at both ends, such as —$CH_2CH_2$— and —$CH_2CH_2CH_2$—. "Alkenyl" means a carbon chain which contains at least one carbon-carbon double bond, and which may be linear or branched or combinations thereof such that $C_{2-6}$alkenyl is defined to identify the group as having 2, 3, 4, 5 or 6 carbons which incorporates at least one double bond, which may be in a E- or a Z-arrangement, including vinyl, allyl, isopropenyl, pentenyl, hexenyl, heptenyl, 1-propenyl, 2-butenyl, 2-methyl-2-butenyl, and the like. "Alkynyl" means a carbon chain which contains at least one carbon-carbon triple bond, and which may be linear or branched or combinations thereof, such as ethynyl, propargyl, 3-methyl-1-pentynyl, 2-heptynyl and the like. "Cycloalkyl" means a mono-, bi- or tri-cyclic structure, optionally combined with linear or branched structures, having the indicated number of carbon atoms, such as cyclopropyl, cyclopentyl, cycloheptyl, adamantyl, cyclododecylmethyl, 2-ethyl-1-bicyclo[4.4.0]decyl, and the like. "Alkoxy" means an alkoxy group of a straight or branched chain having the indicated number of carbon atoms. $C_{1-6}$alkoxy, for example, includes methoxy, ethoxy, propoxy, isopropoxy, and the like.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle, heterocycle, or heterocyclic, as used herein, represents a stable 5- to 7-membered monocyclic or stable 8- to 11-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyran, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, tetrahydropyran, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain embodiments, the heterocyclic group is a heteroaryl group. As used herein, the term "heteroaryl" refers to groups having 5 to 14 ring atoms, preferably 5, 6, 9, or 10 ring atoms; having 6, 10, or 14π electrons shared in a cyclic array; and having, in addition to carbon atoms, between one and about three heteroatoms selected from the group consisting of N, O, and S. Heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof. Examples of saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

In certain other embodiments, the heterocyclic group is fused to an aryl or heteroaryl group. Examples of such fused heterocycles include, without limitation, tetrahydroquinolinyl and dihydrobenzofuranyl.

The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds are useful in a method of treating a neurological or psychiatric disorder associated with PDE2 dysfunction in a patient such as a mammal in need of such inhibition comprising the administration of an effective amount of the compound. In addition to primates, especially humans, a variety of other mammals can be treated according to the method of the present invention. The subject compounds are useful in a method of inhibiting PDE2 activity in a patient such as a mammal in need of such inhibition comprising the administration of an effective amount of the compound. The subject compounds are also useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 dysfunction in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to ameliorate or eliminate unwanted cellular signaling within this site. Without wishing to be bound by any theory, Applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment the compounds of this invention there is provided a method for treating or ameliorating diseases or conditions in neuronal development, learning, and memory prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE10 and/or PDE11A.

Phosphodiesterase enzymes including PDE2 have been implicated in a wide range of biological functions. This has suggested a potential role for these enzymes in a variety of disease processes in humans or other species. The compounds of the present invention have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Pronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphosphate ester bond of a cyclic nucleotide. Any compound exhibiting a Ki (inhibitory constant) below 1 μM would be considered a PDE2 inhibitor as defined herein.

In a typical experiment the PDE2 inhibitory activity of the compounds of the present invention was determined in accordance with the following experimental method. Rhesus PDE2A3 was amplified from rhesus macaque brain cDNA (Biochain Institue, Hayward, Calif.) using primers based on human PDE2A sequence (accession NM_002599.3) where the forward primer containing a Kozak consensus was 5'-gccaccatggggcaggcatgtggc-3' and the reverse primer was 5'-tcactcagcatcaaggagca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) according to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product

R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki~0.2 nM) at 1 µM concentration for 100% inhibition. Bay 60-7550 was obtained from Axxora via Fisher Scientific (cat#ALX-270-421-M025/cat#NC9314773). Put another way, any compound with Ki of ~0.2 to about 2 nM could be used at 1 to 10 µM. 0% of inhibition is determined by using DMSO (1% final concentrations).

A Labcyte Echo 555 (Labcyte, Sunnyvale, Calif.) is used to dispense 200 mL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product #R7506 from Molecular Devices) and the activator cGMP (1 uM final concentration), prepared in the assay buffer (10 mM Tris HCl, pH 7.2, 10 mM MgCl$_2$, 0.05% NaN$_3$ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

Polarization (mP)=1000*(S/So−P/Po)/(S/So+P/Po).

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1=> same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\% \ mP - 100\% \ mP)(Imax - Imin)}{1 + \left[\frac{[Drug]}{\left(10^{-pK_I}\left(1 + \frac{[Substrate]}{K_M}\right)\right)}\right]^{nH}} +$$

$$100\% \ mP + (0\% \ mP - 100\% \ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of ~10 uM was used.

Selectivity for PDE2, as compared to other PDE families, was assessed using the IMAP® technology. Rhesus PDE2A3 and Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or PAM-labeled cGMP from Molecular Devices (Sunnyvale, Calif., product #R7506 or cGMP#R7508), at a final concentration of 50 nM were made in the assay buffer (10 mM Tris HCl, pH 7.2, 10 mM MgCl$_2$, 0.05% NaN$_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE 1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE10 inhibitory activity of a compound which may be used in accordance with the present invention may be determined by these assays.

The compounds of the following examples had activity in inhibiting the human PDE2 enzyme in the aforementioned assays with a Ki of less than about 10 µM. Many of compounds within the present invention had activity in inhibiting the human PDE2 enzyme in the aforementioned assays, with an Ki of less than about 0.1 µM. Additional data is provided in the following Examples. Such a result is indicative of the intrinsic activity of the compounds in use as inhibitors of the PDE2 enzyme. In general, one of ordinary skill in the art would appreciate that a substance is considered to effectively inhibit PDE2 activity if it has a Ki of less than or about 1 μM, preferably less than or about 0.1 μM. The present invention also includes compounds within the generic scope of the invention which possess activity as inhibitors of other phosphodiesterase enzymes.

The subject compounds are further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychoties, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, $5\text{-HT}_{1A}$ agonists or antagonists, especially $5\text{-HT}_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage for is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; Boc: tert-butyloxycarbonyl; DIPEA: N,N-diisopropylethylamine; DPPA: diphenylphosphorylazide; EDC: N-(3-Dimethylaminopropyl)-N'-ethylcarbodiimide; EtOAc: ethyl acetate; HOBt: hydroxybenzotriazole hydrate; TEA: triethylamine; DMF: N,N-dimethylformamide; rt: room temperature; HPLC: high performance liquid chromatography; NMR: nuclear magnetic resonance; TLC: thin-layer chromatography.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

The 2-quinolinones described herein can be synthesized in a straightforward manner by those skilled in the art. Possible synthetic routes are illustrated and described below with specific examples (Scheme A furnishes example 1-57; Scheme B yields example 1-51).

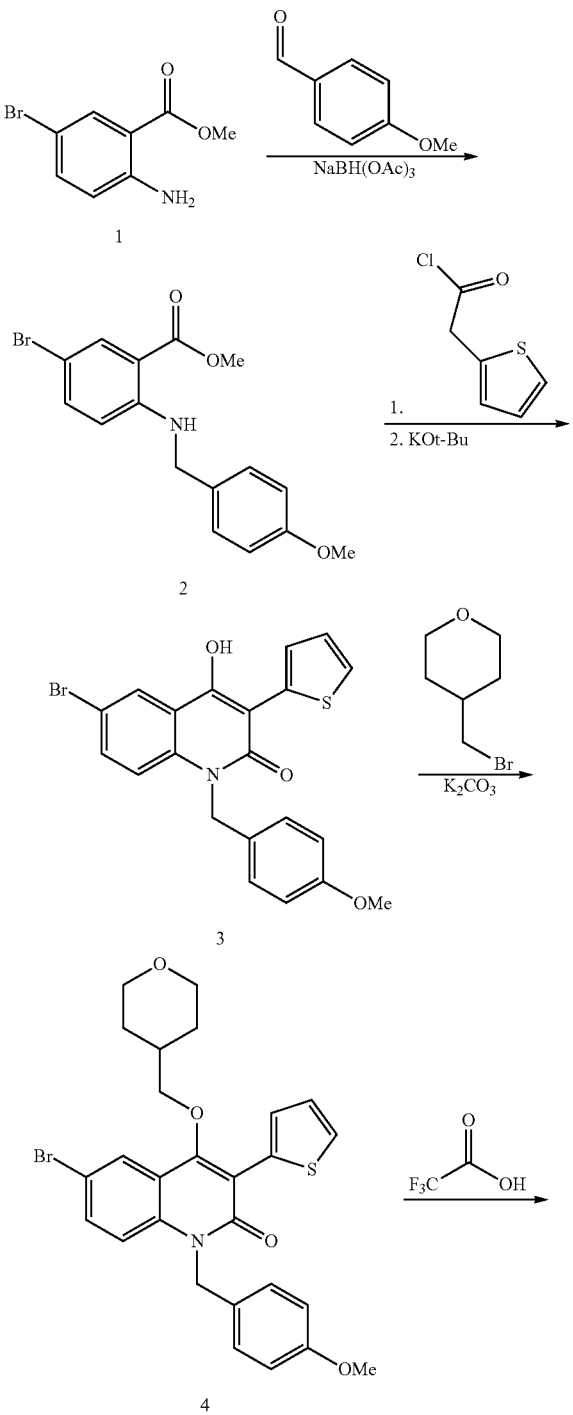

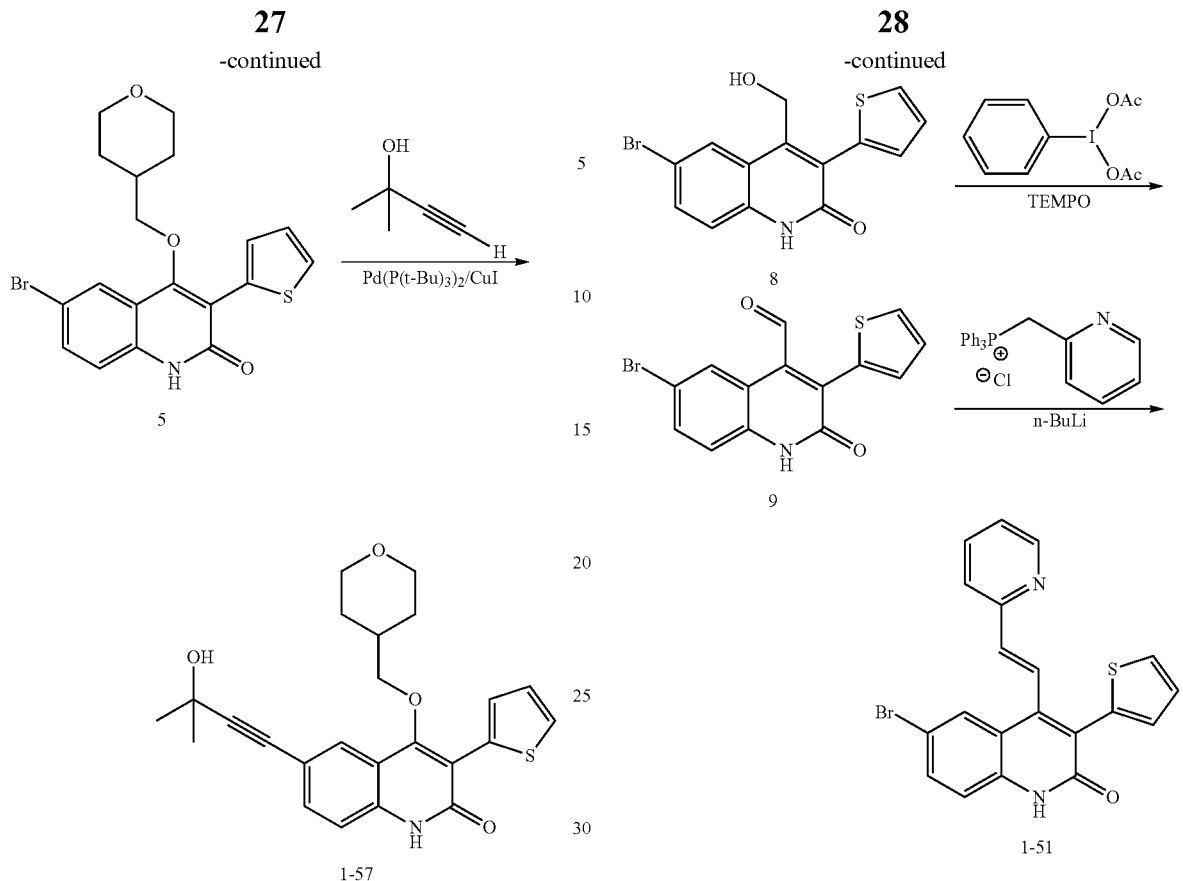

Protection of starting material 1 via reductive amination with p-methoxy benzaldehyde under standard conditions yields PMB protected aniline 2. Subsequent acylation with 2-thiophene acetic acid chloride followed by base mediated ring closure furnishes quinolinone intermediate 3. Alkylation of the free alcohol by treatment with alkyl halide and base provides ether 4. Acid mediated deprotection provides versatile intermediate 5. Finally a palladium-catalyzed coupling reaction yields quinolinone 1-57.

Combination of bromo-isatin 6 and thiophene acetic acid in the presence of sodium acetate furnishes quinolinone 7. Reduction by addition of isobutyl chloroformate and sodium borohydride affords primary alcohol 8. Oxidation employing bisacetoxy iodobenzene and TEMPO yields aldehyde 9. The combination of a phosphonium salt and base in a Wittig reaction provides final quinolinone 1-51.

Reaction Scheme B

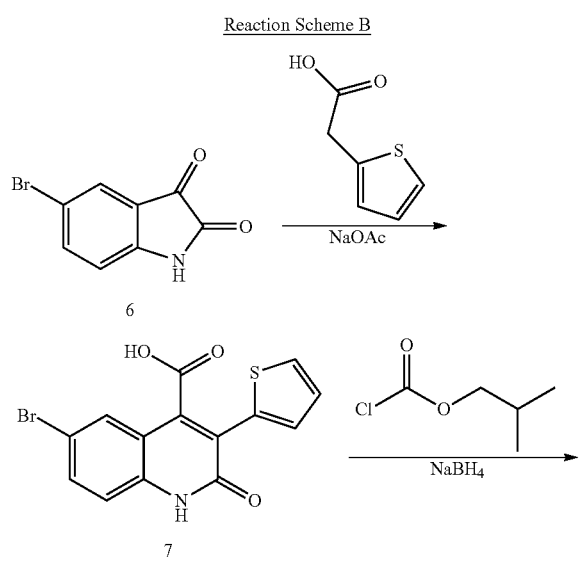

Reaction Scheme C

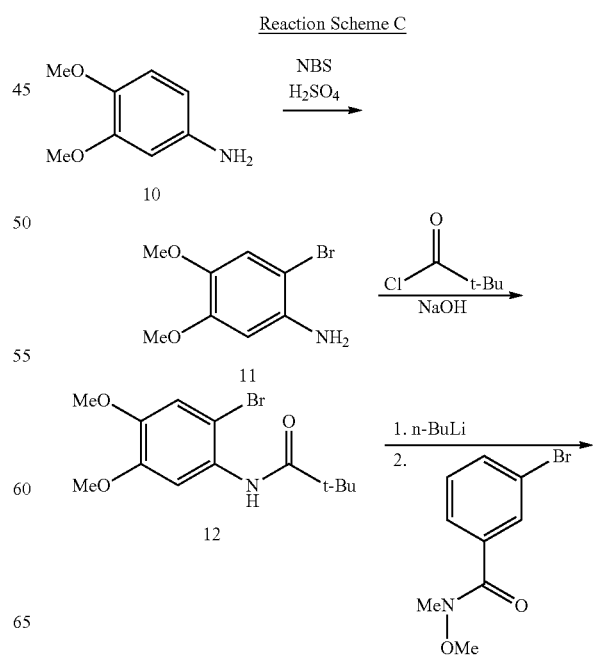

-continued

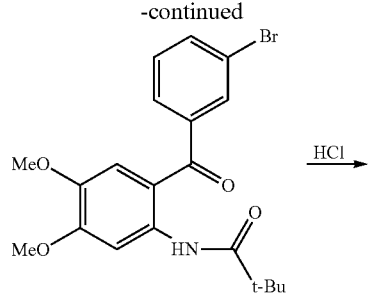

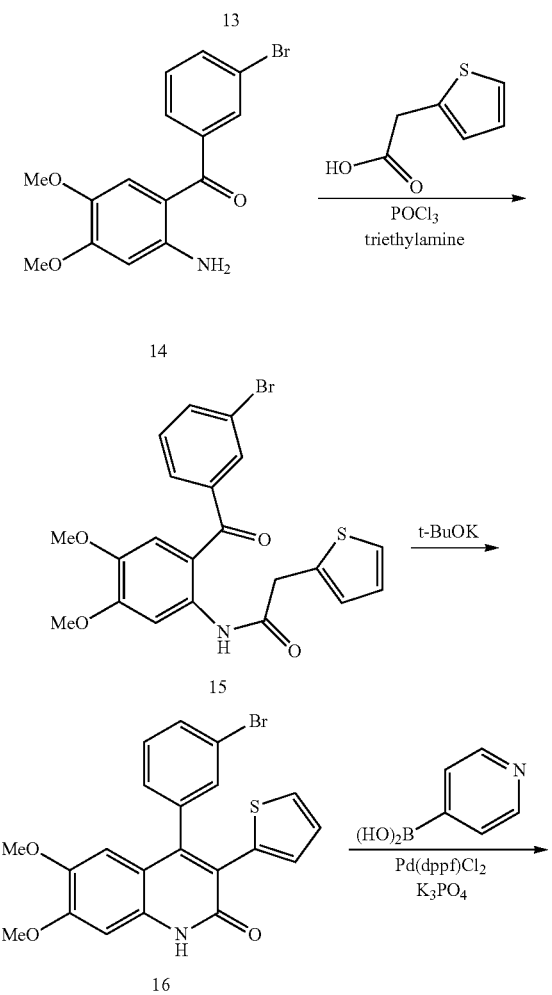

Treatment of aniline 10 with NBS and sulfuric acid affords brominated aniline 11. Amide 12 is formed by combination with pivaloyl chloride. Ketone 13 is accessed by formation of the aryl lithium and combination with the Weinreb amide. The amide bond is cleaved by treatment with hydrochloric acid yielding keto-aniline 14. This intermediate is combined with in situ generated of thiophene acetic acid chloride to furnish amide 15. Base mediated ring-closure leads to quinilinone 16, which then undergoes a Suzuki reaction to afford 1-80.

Example 1-57

4-(tetrahydro-2H-pyran-4-ylmethoxy)-6-(3-hydroxy-3-methylbut-1-yn-1-yl)-3-(thiophen-2-yl)quinolin-2(1H)-one

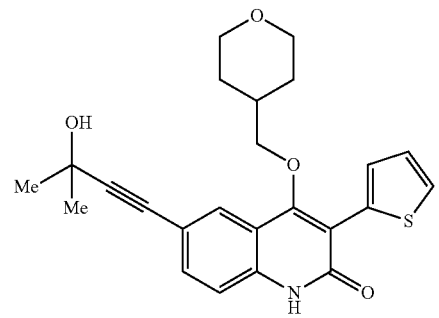 [SMILES: CC(C)(O)C#Cc1ccc2[nH]c(=O)c(-c3cccs3)c(OCC3CCOCC3)c2c1]

Step 1: Methyl 5-bromo-2-[(4-methoxybenzyl)amino]benzoate

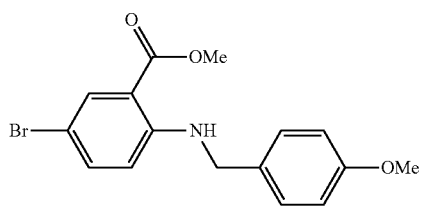 [SMILES: COC(=O)c1cc(Br)ccc1NCc1ccc(OC)cc1]

To a solution of methyl 2-amino-5-bromobenzoate (10.0 g, 43.5 mmol) in dichloromethane (0.5 M, 90 mL) at 0° C. were added p-anisaldehyde (7.9 mL, 65 mmol) and acetic acid (1.2 mL, 22 mmol). Sodium triacetoxyborohydride (18.4 g, 87.0 mmol) was added portion-wise to the solution mixture. The reaction was allowed to warm to room temp and stirred overnight. Upon completion, the reaction was poured into saturated sodium bicarbonate (200 mL). The product was extracted with dichloromethane (3×75 mL). The combined organic extractions were dried over magnesium sulfate, filtered, and concentrated in vacuo. The crude material was purified via flash chromatography (silica, 1:1 hexanes/dichloromethane) to yield methyl 5-bromo-2-[(4-methoxybenzyl)amino]benzoate. HRMS (M+H)=350.0381. $^1$H NMR (400 MHz, CDCl$_3$) 8.08 (b, 1H), 8.10 (d, 1H), 7.36 (dd, 1H), 7.24 (d, 2H), 6.88 (d, 2H), 6.54 (d, 1H), 4.35 (s, 2H), 3.86 (s, 3H), 3.80 (s, 3H).

Step 2: 6-bromo-4-hydroxy-1-(4-methoxybenzyl)-3-(thiophen-2-yl)quinolin-2(1H)-one

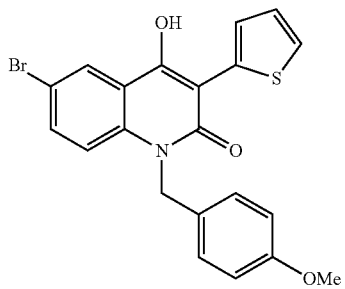 [SMILES: COc1ccc(Cn2c(=O)c(-c3cccs3)c(O)c3cc(Br)ccc32)cc1]

To a solution of methyl 5-bromo-2-[(4-methoxybenzyl)amino]benzoate (2.0 g, 5.7 mmol) in dichloromethane (0.50 M, 11 mL) at room temp were added triethylamine (1.6 mL, 11 mmol) and 2-thiophenylacetyl chloride (1.1 g, 6.9 mmol), followed by addition of DMAP (35 mg, 5.0 mol %). The reaction was left stirring overnight. Additional portions of 2-thiophenylacetyl chloride were added until the complete consumption of starting material was observed. The crude reaction mixture was poured in neutral water (100 mL). The product was extracted with dichloromethane (3×50 mL). The combined organic extractions were dried over magnesium sulfate, filtered, and concentrated in vacuo to furnish methyl 5-bromo-2-[(4-methoxybenzyl)(thiophen-2-ylacetyl)amino]benzoate as an orange oil. Used without further purification. LCMS (M+1)=473.7.

Methyl 5-bromo-2-[(4-methoxybenzyl)(thiophen-2-ylacetyl)amino]benzoate (2.7 g, 5.7 mmol) was taken into tetrahydrofuran (0.50 M, 11 mL) and to this solution was added potassium tert-butoxide (1.3 g, 11 mmol) at room temp. The reaction was stirred for an hour. The crude reaction mixture was poured into 1 N HCl aq. (100 mL). The product was extracted with ethyl acetate (3×50 mL). The combined organic extractions were dried over magnesium sulfate, filtered, and concentrated in vacuo to yield 6-bromo-4-hydroxy-1-(4-methoxybenzyl)-3-(thiophen-2-yl)quinolin-2(1H)-one as a brown oil. Used without further purification. LCMS (M+H)=441.6.

Step 3: 6-bromo-4-(tetrahydro-2H-pyran-4-ylmethoxy)-1-(4-methoxybenzyl)-3-(thiophen-2-yl)quinolin-2(1H)-one

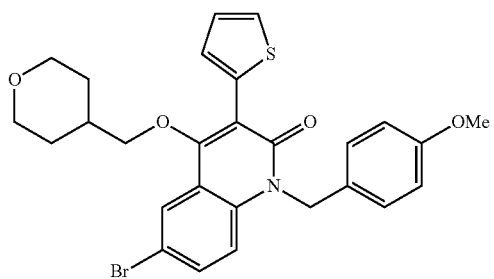 [SMILES: COc1ccc(Cn2c(=O)c(-c3cccs3)c(OCC3CCOCC3)c3cc(Br)ccc32)cc1]

To a solution of 6-bromo-4-hydroxy-1-(4-methoxybenzyl)-3-(thiophen-2-yl)quinolin-2(1H)-one (1.2 g, 2.8 mmol) in tetrahydrofuran (0.3 M, 10 mL) at room temp was added potassium carbonate (1.2 g, 8.4 mmol). 4-bromomethyl tetrahydropyran (1.0 g, 5.6 mmol) was added to this solution mixture. The reaction mixture was left stirring overnight. The crude reaction mixture was poured into 1 N sodium hydroxide (100 mL). The product was extracted with ethyl acetate (3×50 mL). The combined organic extractions were dried over magnesium sulfate, filtered, and concentrated in vacuo. The crude material was purified via flash chromatography (silica, 7:3 hexanes/ethyl acetate) to yield 6-bromo-4-(tetrahydro-2H-pyran-4-ylmethoxy)-1-(4-methoxybenzyl)-3-(thiophen-2-yl)quinolin-2(1H)-one as an orange oil. LCMS (M+H)=539.8.

Step 4: 6-bromo-4-(tetrahydro-2H-pyran-4-ylmethoxy)-3-(thiophen-2-yl)quinolin-2(1H)-one

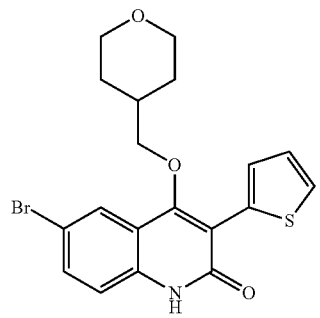 [SMILES: O=c1[nH]c2ccc(Br)cc2c(OCC2CCOCC2)c1-c1cccs1]

6-bromo-4-(tetrahydro-2H-pyran-4-ylmethoxy)-1-(4-methoxybenzyl)-3-(thiophen-2-yl)quinolin-2(1H)-one (160 mg, 0.30 mmol) was taken into neat trifluoroacetic acid (500 µL, 6.5 mmol). The reaction mixture was heated overnight at 100° C. The crude reaction mixture was poured into saturated sodium bicarbonate (50 mL). The product was extracted with dichloromethane (3×50 mL). The combined organic extractions were dried over magnesium sulfate, filtered, and concentrated in vacuo. The crude material was purified via flash chromatography (silica, 4:1 dichlormethane/ethyl acetate) to yield 6-bromo-4-(tetrahydro-2H-pyran-4-ylmethoxy)-3-(thiophen-2-yl)quinolin-2(1H)-one as an off white solid. LCMS (M+H)=419.8. $^1$H NMR (400 MHz, CDCl$_3$) 12.0 (s, 1H), 8.00 (s, 1H), 7.88 (d, 1H), 7.62 (d, 1H), 7.54 (d, 1H) 7.30 (d, 1H), 7.18 (t, 1H), 4M (dd, 2H) 3.65 (d, 2H), 3.45 (t, 2H), 2.15 (m, 1H), 1.75 (d, 2H), 1.4 (m, 2H).

Step 5: 4-(tetrahydro-2H-pyran-4-ylmethoxy)-6-(3-hydroxy-3-methylbut-1-yn-1-yl)-3-(thiophen-2-yl)quinolin-2(1H)-one

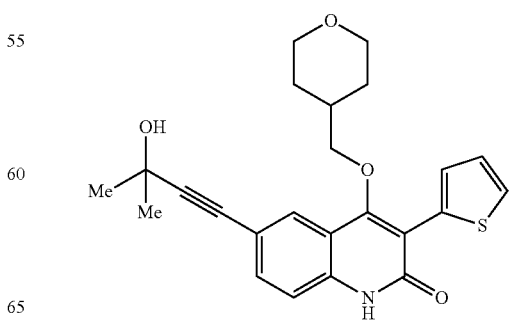

A 5 mL microwave vial was charged with a magnetic stir bar, 6-bromo-4-(tetrahydro-2H-pyran-4-ylmethoxy)-3-(thiophen-2-yl)quinolin-2(1H)-one (22 mg, 52 mop, copper (I) iodide (1.0 mg, 5.0 mop, and bis(tri-t-butylphosphine)palladium(0) (1.0 mg, 3.0 μmol). The vessel was sealed. The contents of the vessel were dried under high vacuum, and flushed with nitrogen. Acetonitrile (500 μL) was added under nitrogen followed by addition of 2-methyl-3-butyn-2-ol (18 mg, 210 μmol), and diisopropylethyl amine (46 μL, 260 μmol). The reaction was heated to 100° C. in an oil bath for 3 h. The crude product was purified by reverse-phase chromatography to yield 4-(tetrahydro-2H-pyran-4-ylmethoxy)-6-(3-hydroxy-3-methylbut-1-yn-1-yl)-3-(thiophen-2-yl)quinolin-2(1H)-one as off white solid. LCMS (M+H)=423.9. $^1$H NMR (400 MHz, CDCl$_3$) 11.0 (s, 1H), 7.90 (s, 1H), 7.84 (d, 1H), 7.52 (m, 2H), 7.24 (1H), 7.18 (t, 1H), 4.00 (dd, 2H) 3.65 (d, 2H), 3.45 (t, 2H), 2.15 (m, 1H), 1.75 (d, 2H), 1.65 (s, 6H), 1.50-1.40 (m, 3H).

Example 1-51

6-bromo-4-[(E/Z)-2-(pyridine-2-yl)ethenyl]-3-(thiophen-2-yl)quinolin-2(1H)-one

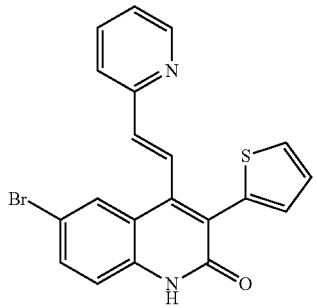

Step 1: 6-bromo-2-oxo-3-(thiophene-2-yl)-1,2-dihydroquinoline-4-carboxylic acid

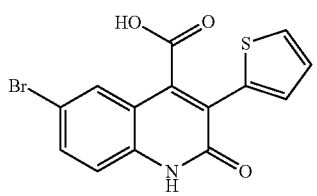 [SMILES: O=C(O)c1c(-c2cccs2)c(=O)[nH]c2ccc(Br)cc12]

To a flask containing 2-thiophene acetic acid (3.08 g, 21.7 mmol) at 150° C. were added sodium acetate (0.25 g, 3.1 mmol) and 7-bromoisatin (2.80 g, 12.4 mmol). The reaction was allowed to stir at elevated temperatures for 1 h. The reaction was cooled to room temperature and diluted with ethanol (50 ml). The reaction was placed in an ice bath for 30 min. The product was collected by filtration and rinsed with cold ethanol (20 ml). The beige solid was dried in vacuo to afford 6-bromo-2-oxo-3-(thiophene-2-yl)-1,2-dihydroquinoline-4-carboxylic acid. Compound used without further purification. LCMS (M+H)=3513.

Step 2: 6-bromo-4-(hydroxymethyl)-3-(thiophen-2-yl)quinolin-2(1H)-one

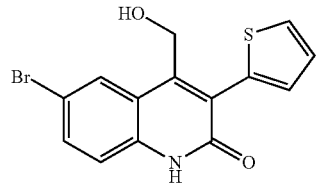 [SMILES: O=c1[nH]c2ccc(Br)cc2c(CO)c1-c1cccs1]

To a solution containing 6-bromo-2-oxo-3-(thiophene-2-yl)-1,2-dihydroquinoline-4-carboxylic acid (1.00 g, 2.86 mmol) in tetrahydrofuran (11.4 ml) were added isobutyl chloroformate (0.364 ml, 2.86 mmol) and triethylamine (0.398 ml, 2.86 mmol) at 0° C. The reaction was allowed to stir at room temperature for 30 min. The reaction was then filtered to remove solids and placed in an ice bath at 0° C. Sodium borohydride (0.119 g, 3.14 mmol) was added to the reaction mixture followed by methanol (3 ml). This mixture was allowed to warm to room temperature and stirred for 4 h. The reaction was diluted in ethyl acetate (50 ml) and extracted with 1 N sodium hydroxide (3×40 ml) and sodium chloride (1×40 ml). The organic layer was dried over magnesium sulfate, filtered and concentrated to afford 6-bromo-4-(hydroxymethyl)-3-(thiophen-2-yl)quinolin-2(1H)-one as a crude, yellow oil. Compound used without further purification. LCMS (M+H)=337.7.

Step 3: 6-bromo-2-oxo-3-(thiophen-2-yl)-1,2-dihydroquinoline-4-carbaldehyde

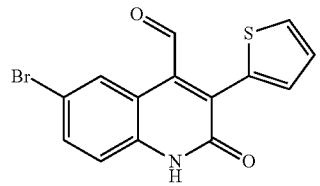 [SMILES: O=Cc1c(-c2cccs2)c(=O)[nH]c2ccc(Br)cc12]

To a solution of 6-bromo-4-(hydroxymethyl)-3-(thiophen-2-yl)quinolin-2(1H)-one (0.155 g, 0.461 mmol) in acetonitrile (4.60 ml) were added bisacetoxy iodobenzene (0.134 g, 0.415 mmol) and 2,2,6,6-tetramethyl piperidin-1-oxyl (7.30 mg, 0.046 mmol). The reaction was allowed to stir at room temperature for 16 h. The reaction was diluted with ethyl acetate (30 ml) and extracted with saturated sodium thiosulfate (1×25 ml), sodium bicarbonate (1×25 ml) and sodium chloride (1×25 ml). The organic layer was dried over magnesium sulfate, filtered and concentrated. Purification of the crude oil by silica chromatography gave 6-bromo-2-oxo-3-(thiophen-2-yl)-1,2-dihydroquinoline-4-carbaldehyde as a white solid. LCMS (M+H)=335.76.

Step 4: 6-bromo-4-[(E)-2-(pyridine-2-yl)ethenyl]-3-(thiophen-2-yl)quinolin-2(1H)-one

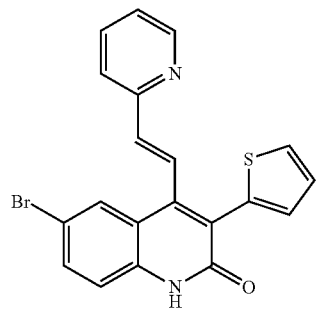 [SMILES: O=c1[nH]c2ccc(Br)cc2c(/C=C/c2ccccn2)c1-c1cccs1]

To a solution containing triphenyl(2-pyridylmethyl)phosphonium chloride hydrochloride (153 mg, 0.359 mmol) in tetrahydrofuran (2.26 ml) at −78° C. was added n-butyl lithium (2.50 M, 0.685 mmol). This mixture was stirred for 15 min. and then added to a solution containing 6-bromo-2-oxo-3-(thiophen-2-yl)-1,2-dihydroquinoline-4-carbaldehyde (109 mg, 0.326 mmol) in tetrahydrofuran (1 ml) at −78° C. The reaction was allowed to stir for 4 h at room temperature. The reaction was quenched with 1 N hydrochloric acid (10 ml) and then the pH was increased with 1 N sodium hydroxide. This mixture was extracted with ethyl acetate (3×30 ml). The organic layers were combined and extracted with sodium chloride (1×25 ml). The organic layer was then dried over magnesium sulfate, filtered and concentrated. The resulting crude solid was purified by reverse phase chromatography to afford 6-bromo-4-[(E)-2-(pyridine-2-yl)ethenyl]-3-(thiophen-2-yl)quinolin-2(1H)-one as a yellow solid. LCMS (M+H)=410.69. $^1$H NMR (400 MHz, d$_6$-DMSO) δ 12.28 (s, 1H), 8.63-8.60 (m, 1H), 7.95 (d, 1H), 7.85 (m, 1H), 7.74-7.65 (m, 3H), 7.60 (d, 1H), 7.39-7.33 (m, 3H), 7.09 (dd, 1H), 6.99 (d, 1H).

Example 1-80

6,7-dimethoxy-4-[3-(pyridin-4-yl)phenyl]-3-(thiophen-2-yl)quinolin-2(1H)-one

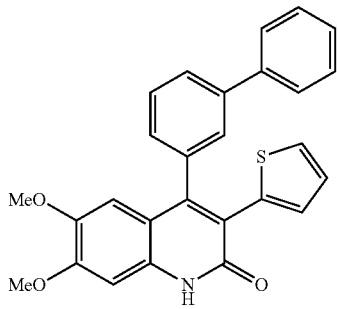 [SMILES: COc1cc2[nH]c(=O)c(-c3cccs3)c(-c3cccc(-c4ccccc4)c3)c2cc1OC]

Step 1: 2-bromo-4,5-dimethoxyaniline

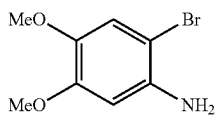

To a solution of 3,4-dimethoxybenzenamine (20.0 g, 0.130 mol) in dry THF (200 mL) was added concentrated H$_2$SO$_4$ (20 drops) under N$_2$ at −78° C. After 10 mains, NBS (23.2 g, 0.130 mol) was added in potions at −78° C. Then the reaction mixture was allowed to gradually warm up to room temperature over 1 hour. THF was removed under reduced pressure. The residue was diluted with EtOAc (200 mL), and washed with water (80 mL×3). The organic layer was dried over anhydrous MgSO$_4$, filtered and concentrated in vacuum. The residue was purified by silica gel column (15:1 hexanes/ethyl acetate) to afford 2-bromo-4,5-dimethoxyaniline as a yellow solid. MS (M+H)=232 and 234.

Step 2: N-(2-bromo-4,5-dimethoxyphenyl)-2,2-dimethylpropanamide

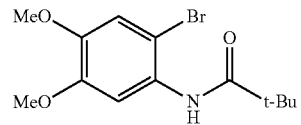

A dry 500 mL three-necked flask was charged with 2-bromo-4,5-dimethoxyaniline (23.4 g, 0.10 mol) and t-BuOMe (200 mL), NaOH (25.3 g, 25%, 0.158 mol) was added in portions at 0° C. Then pivaloyl chloride (12.9 g, 0.106 mol) was added dropwise slowly under N$_2$ at 0° C. After addition, the mixture was stirred for an additional 1 hour and diluted with water (100 mL), acidified by 5% HCl to pH=7 and extracted with EtOAc (100 mL×3). The combined organic layers were washed with water (100 mL×3), dried over anhydrous MgSO$_4$, filtrated and concentrated in vacuum to afford the compound N-(2-bromo-4,5-dimethoxyphenyl)-2,2-dimethylpropanamide. MS (M+H)=316 and 318.

Step 3: N-{2-[(3-bromophenyl)carbonyl]-4,5-dimethoxyphenyl}-2,2-dimethylpropanamide

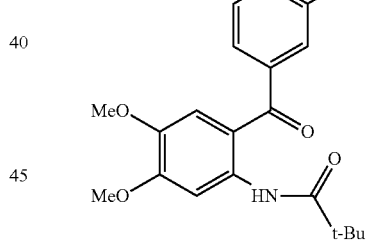

A flamed dried 500 mL three-necked flask was charged N-(2-bromo-4,5-dimethoxyphenyl)-2,2-dimethylpropanamide (30 g, 95 mmol) and dry THF (200 mL) under N$_2$. n-BuLi (114 mL, 2.5 mol/L, 285 mmol) was added dropwise at −78° C. After the mixture was stirred at −78° C. for 1 hour, 3-bromo-N-methoxy-N-methylbenzamide (23.2 g, 94.9 mmol) in dry THF (30 mL) was added dropwise slowly at −78° C. The resulting mixture was stirred at −78° C. for 3 hours, then quenched with saturated NH$_4$Cl (100 mL). The mixture was exacted with EtOAc (100 mL×3). The combined organic phases were dried over anhydrous MgSO$_4$, filtered and concentrated under reduced pressure. The residue was purified by silica gel column (30:1 hexanes/ethyl acetate) to afford a N-{2-[(3-bromophenyl)carbonyl]-4,5-dimethoxyphenyl}-2,2-dimethylpropanamide as a yellow solid. MS (M+H)=420 and 422.

Step 4: (2-amino-4,5-dimethoxyphenyl)(3-bromophenyl)methanone

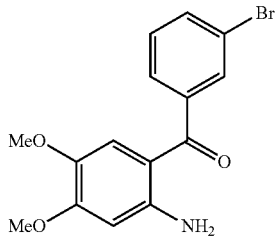 [SMILES: COc1cc(N)c(C(=O)c2cccc(Br)c2)cc1OC]

To a solution of N-{2-[(3-bromophenyl)carbonyl]-4,5-dimethoxyphenyl}-2,2-dimethylpropanamide (7.9 g, 18.9 mmol) in 1,4-dioxane (80 mL) was added concentrated HCl (9.55 g, 94.2 mmol). The mixture was refluxed for 2 hours. After cooling to room temperature, 1,4-dioxane was removed in vacuum and the residue was diluted with water (100 mL) and EtOAc (100 mL), then neutralized with NaHCO$_3$ to pH=8. The mixture was extracted with EtOAc (80 mL×3). The combined organic phases were dried over anhydrous MgSO$_4$, filtered and concentrated under vacuum to afford (2-amino-4,5-dimethoxyphenyl)(3-bromophenyl)methanone. MS (M+H)=336 and 338.

Step 5: N-{2-[(3-bromophenyl)carbonyl]-4,5-dimethoxyphenyl}-2-(thiophen-2-yl)acetamide

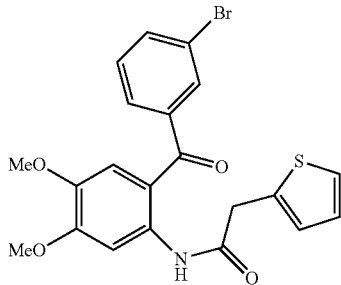 [SMILES: COc1cc(NC(=O)Cc2cccs2)c(C(=O)c2cccc(Br)c2)cc1OC]

To a solution of (2-amino-4,5-dimethoxyphenyl)(3-bromophenyl)methanone (5 g, 14.9 mmol) in dry DCM (125 mL) was added thiophen-2-ylacetic acid (2.54 g, 17.9 mmol) and Et$_3$N (6.77, 66.9 mmol) at 0° C. in N$_2$. 10 minutes later, POCK (3.4 g, 22.31 mmol) was added dropwise at 0° C. in N$_2$. The reaction mixture was stirred for 1 hour at 0° C. and then quenched with saturated NaHCO$_3$, and neutralized to pH=8. The mixture was exacted with ACM (30 mL×3). The combined organic layer was dried over anhydrous MgSO$_4$, filtered and concentrated under vacuum to afford N-{2-[(3-bromophenyl)carbonyl]-4,5-dimethoxyphenyl}-2-(thiophen-2-yl)acetamide. MS (M+H)=460 and 462.

Step 6: 4-(3-bromophenyl)-6,7-dimethoxy-3-(thiophen-2-yl)quinolin-2(1H)-one

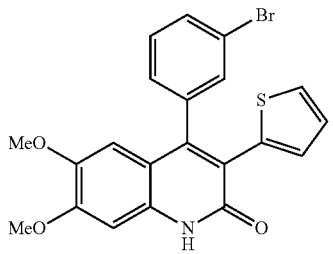 [SMILES: COc1cc2[nH]c(=O)c(-c3cccs3)c(-c3cccc(Br)c3)c2cc1OC]

To a solution of N-{2-[(3-bromophenyl)carbonyl]-4,5-dimethoxyphenyl}-2-(thiophen-2-yl)acetamide (8 g, 17.4 mmol) in dry THF (80 mL) was added t-BuOK (6 g 52.1 mmol) in portions at 0° C. The reaction mixture was stirred for 1 hour and concentrated under reduced pressure. The residue was diluted with EtOAc (50 mL). The combined organic layers were dried over anhydrous MgSO$_4$, filtered and concentrated in vacuum to afford 4-(3-bromophenyl)-6,7-dimethoxy-3-(thiophen-2-yl)quinolin-2(1H)-one. MS (M+H)=442 and 444.

Step 7: 6,7-dimethoxy-4-[3-(pyridin-4-yl)phenyl]-3-(thiophen-2-yl)quinolin-2(1H)-one

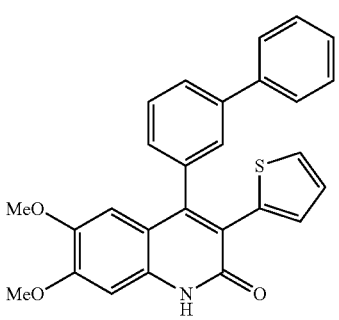 [SMILES: COc1cc2[nH]c(=O)c(-c3cccs3)c(-c3cccc(-c4ccccc4)c3)c2cc1OC]

To a solution of 4-(3-bromophenyl)-6,7-dimethoxy-3-(thiophen-2-yl)quinolin-2(1H)-one (30 mg, 0.068 mmol) in EtOH (0.5 mL)/H$_2$O (0.5 mL)/toluene (0.5 mL) were added phenyl boronic acid (13 mg, 0.10 mmol), Cs$_2$CO$_3$ (66 mg, 0.20 mmol) and Pd(PPh)$_4$ (4 mg, 0.003 mmol). The resulting mixture was stirred at 100° C. for 18 hours under N$_2$. Cooled to room temperature, EtOH and toluene were removed under reduced pressure. The residue was diluted with EtOAc (10 mL), washed with water (10 mL×3), dried with MgSO$_4$, filtered and concentrated under vacuum. The residue was purified by reverse-phase HPLC to afford 6,7-dimethoxy-4-[3-(pyridin-4-yl)phenyl]-3-(thiophen-2-yl)quinolin-2(1H)-one. MS (M+H)=440. $^1$H NMR (400 MHz, d$_6$-DMSO) δ 11.85 (s, 1H), 7.55 (d, 1H), 7.42 (d, 2H), 7.36 (t, 1H), 7.319 (s 1H), 7.24 (t, 1H), 7.20-7.15 (m, 2H), 7.06 (d, 1H), 6.78 (s 1H), 6.59 (t, 1H), 6.49 (d, 1H), 6.30 (s, 1H), 3.65 (s 1H), 3.29 (s 1H).

Table 1

The following compounds were prepared using the foregoing methodology, but substituting the appropriately substituted reagent, as described in the foregoing Reaction Schemes and Examples. The requisite starting materials were commercially available, described in the literature, or readily synthesized by one skilled in the art of organic synthesis without undue experimentation. Final products were purified by either gradient elution on SiO$_2$ (EtOAc/hexanes or MeOH/CH$_2$Cl$_2$), reverse phase flash chromatography (MeCN/H$_2$O), or preparative thin layer chromatography (EtOAc/hexanes or MeOH/CH$_2$Cl$_2$ or MeOH/EtOAc), and were isolated as free-bases.

| Cpd. | Structure | Name | Parent MW |
|---|---|---|---|
| 1-1 | 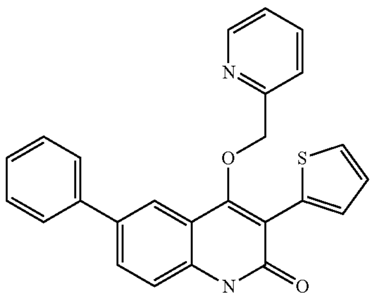 [SMILES: O=c1[nH]c2ccc(-c3ccccc3)cc2c(OCc2ccccn2)c1-c1cccs1] | 6-phenyl-4-(pyridin-2-ylmethoxy)-3-(thiophen-2-yl)quinolin-2(1H)-one | 410.49 |
| 1-2 | 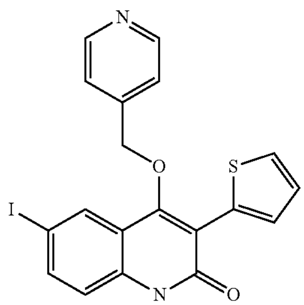 [SMILES: O=c1[nH]c2ccc(I)cc2c(OCc2ccncc2)c1-c1cccs1] | 6-iodo-4-(pyridin-4-ylmethoxy)-3-(thiophen-2-yl)quinolin-2(1H)-one | 460.29 |
| 1-3 | 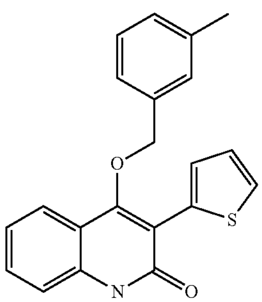 [SMILES: Cc1cccc(COc2c(-c3cccs3)c(=O)[nH]c3ccccc23)c1] | 4-[(3-methylbenzyl)oxy]-3-(thiophen-2-yl)quinolin-2(1H)-one | 347.43 |
| 1-4 | 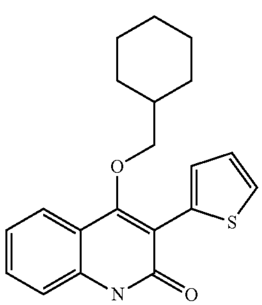 [SMILES: O=c1[nH]c2ccccc2c(OCC2CCCCC2)c1-c1cccs1] | 4-(cyclohexylmethoxy)-3-(thiophen-2-yl)quinolin-2(1H)-one | 339.45 |
| 1-5 | 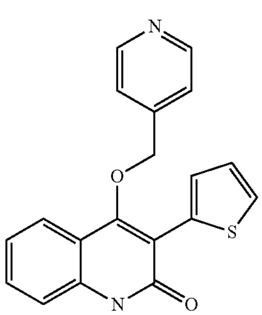 [SMILES: O=c1[nH]c2ccccc2c(OCc2ccncc2)c1-c1cccs1] | 4-(pyridin-4-ylmethoxy)-3-(thiophen-2-yl)quinolin-2(1H)-one | 334.39 |

-continued

| Cpd. | Structure | Name | Parent MW |
| --- | --- | --- | --- |
| 1-6 | 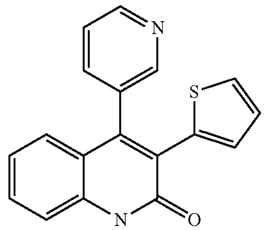 [SMILES: O=c1[nH]c2ccccc2c(-c2cccnc2)c1-c1cccs1] | 4-(pyridin-3-yl)-3-(thiophen-2-yl)quinolin-2(1H)-one | 304.37 |
| 1-7 | 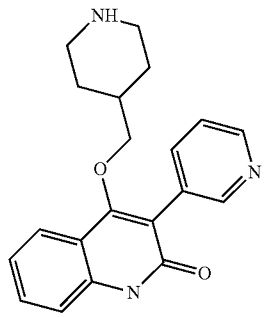 [SMILES: O=c1[nH]c2ccccc2c(OCC2CCNCC2)c1-c1cccnc1] | 4-(piperidin-4-ylmethoxy)-3-(pyridin-3-yl)quinolin-2(1H)-one | 335.40 |
| 1-8 | 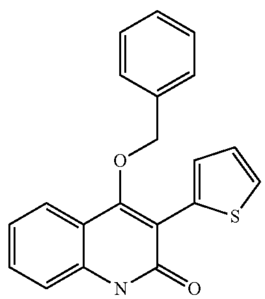 [SMILES: O=c1[nH]c2ccccc2c(OCc2ccccc2)c1-c1cccs1] | 4-(benzyloxy)-3-(thiophen-2-yl)quinolin-2(1H)-one | 333.40 |
| 1-9 | 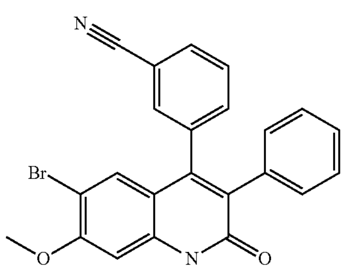 [SMILES: COc1cc2[nH]c(=O)c(-c3ccccc3)c(-c3cccc(C#N)c3)c2cc1Br] | 3-(6-bromo-7-methoxy-2-oxo-3-phenyl-1,2-dihydroquinolin-4-yl)benzonitrile | 431.28 |
| 1-10 | 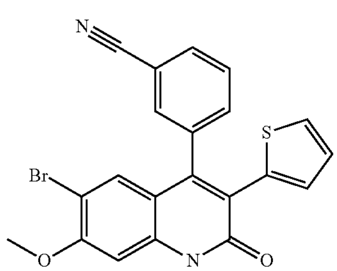 [SMILES: COc1cc2[nH]c(=O)c(-c3cccs3)c(-c3cccc(C#N)c3)c2cc1Br] | 3-[6-bromo-7-methoxy-2-oxo-3-(thiophen-2-yl)-1,2-dihydroquinolin-4-yl]benzonitrile | 437.31 |

-continued

| Cpd. | Structure | Name | Parent MW |
| --- | --- | --- | --- |
| 1-11 | 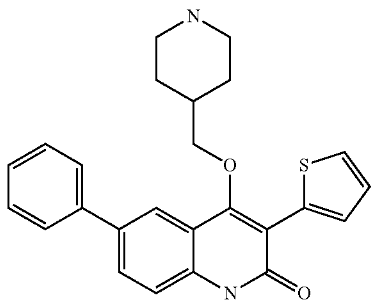 [SMILES: O=c1[nH]c2ccc(-c3ccccc3)cc2c(OCC2CCNCC2)c1-c1cccs1] | 6-phenyl-4-(piperidin-4-ylmethoxy)-3-(thiophen-2-yl)quinolin-2(1H)-one | 417.54 |
| 1-12 | 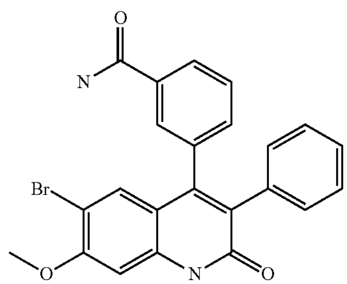 [SMILES: COc1cc2[nH]c(=O)c(-c3ccccc3)c(-c3cccc(C(N)=O)c3)c2cc1Br] | 3-(6-bromo-7-methoxy-2-oxo-3-phenyl-1,2-dihydroquinolin-4-yl)benzamide | 449.30 |
| 1-13 | 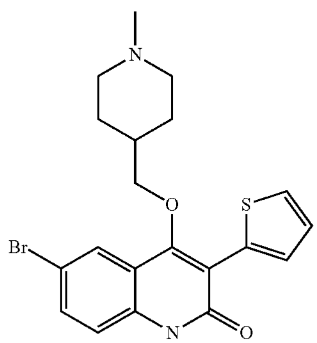 [SMILES: CN1CCC(COc2c(-c3cccs3)c(=O)[nH]c3ccc(Br)cc23)CC1] | 6-bromo-4-[(1-methylpiperidin-4-yl)methoxy]-3-(thiophen-2-yl)quinolin-2(1H)-one | 433.36 |
| 1-14 | 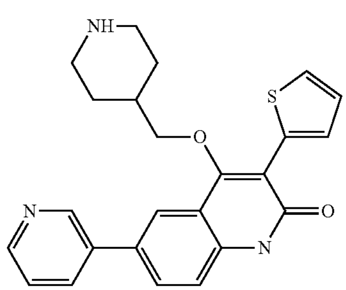 [SMILES: O=c1[nH]c2ccc(-c3cccnc3)cc2c(OCC2CCNCC2)c1-c1cccs1] | 4-(piperidin-4-ylmethoxy)-6-(pyridin-3-yl)-3-(thiophen-2-yl)quinolin-2(1H)-one | 417.52 |
| 1-15 | 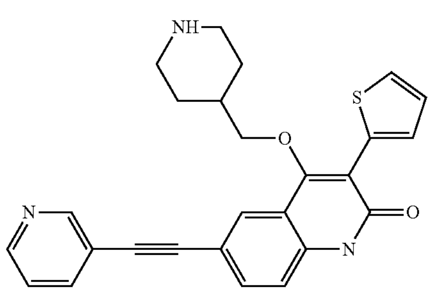 [SMILES: O=c1[nH]c2ccc(C#Cc3cccnc3)cc2c(OCC2CCNCC2)c1-c1cccs1] | 4-(piperidin-4-ylmethoxy)-6-(pyridin-3-ylethynyl)-3-(thiophen-2-yl)quinolin-2(1H)-one | 441.54 |

-continued

| Cpd. | Structure | Name | Parent MW |
|---|---|---|---|
| 1-16 | 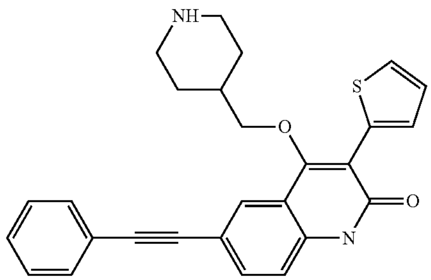 [SMILES: O=c1[nH]c2ccc(C#Cc3ccccc3)cc2c(OCC2CCNCC2)c1-c1cccs1] | 6-(phenylethynyl)-4-(piperidin-4-ylmethoxy)-3-(thiophen-2-yl)quinolin-2(1H)-one | 440.16 |
| 1-17 | 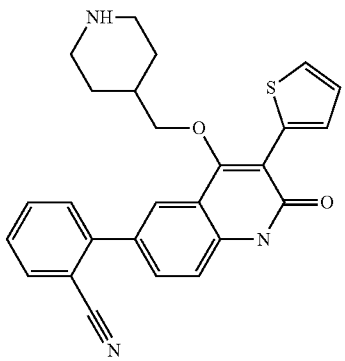 [SMILES: N#Cc1ccccc1-c1ccc2[nH]c(=O)c(-c3cccs3)c(OCC3CCNCC3)c2c1] | 2-[2-oxo-4-(piperidin-4-ylmethoxy)-3-(thiophen-2-yl)-1,2-dihydroquinolin-6-yl]benzonitrile | 441.54 |
| 1-18 | 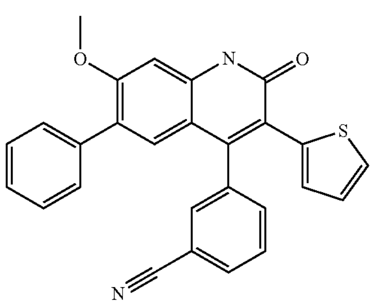 [SMILES: COc1cc2[nH]c(=O)c(-c3cccs3)c(-c3cccc(C#N)c3)c2cc1-c1ccccc1] | 3-[7-methoxy-2-oxo-6-phenyl-3-(thiophen-2-yl)-1,2-dihydroquinolin-4-yl]benzonitrile | 434.51 |
| 1-19 | 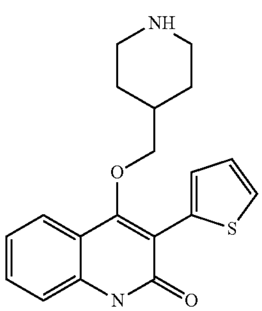 [SMILES: O=c1[nH]c2ccccc2c(OCC2CCNCC2)c1-c1cccs1] | 4-(piperidin-4-ylmethoxy)-3-(thiophen-2-yl)quinolin-2(1H)-one | 340.44 |
| 1-20 | 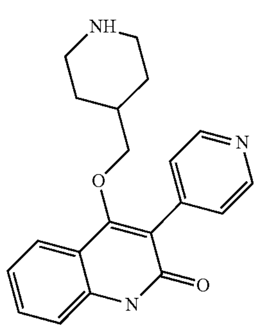 [SMILES: O=c1[nH]c2ccccc2c(OCC2CCNCC2)c1-c1ccncc1] | 4-(piperidin-4-ylmethoxy)-3-(pyridin-4-yl)quinolin-2(1H)-one | 335.40 |

-continued

| Cpd. | Structure | Name | Parent MW |
|---|---|---|---|
| 1-21 | 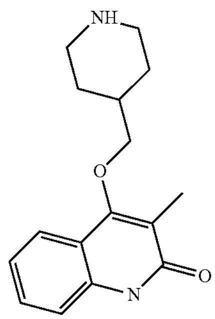 [SMILES: Cc1c(OCC2CCNCC2)c2ccccc2[nH]c1=O] | 3-methyl-4-(piperidin-4-ylmethoxy)quinolin-2(1H)-one | 272.34 |
| 1-22 | 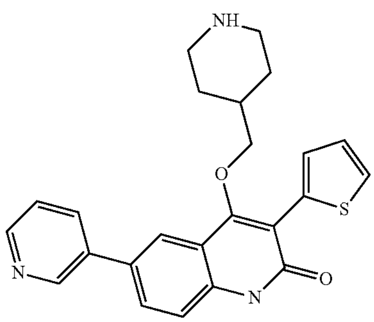 [SMILES: O=c1[nH]c2ccc(-c3cccnc3)cc2c(OCC2CCNCC2)c1-c1cccs1] | 4-(piperidin-4-ylmethoxy)-6-(pyridin-3-yl)-3-(thiophen-2-yl)quinolin-2(1H)-one | 417.52 |
| 1-23 | 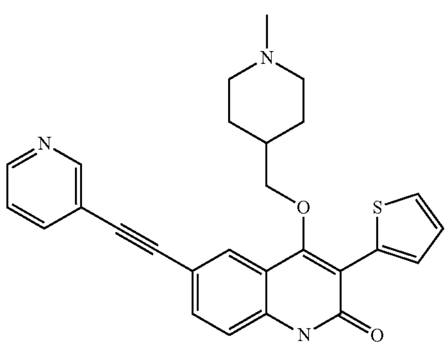 [SMILES: CN1CCC(COc2c(-c3cccs3)c(=O)[nH]c3ccc(C#Cc4cccnc4)cc23)CC1] | 4-[(1-methylpiperidin-4-yl)methoxy]-6-(pyridin-3-ylethynyl)-3-(thiophen-2-yl)quinolin-2(1H)-one | 455.57 |
| 1-24 | 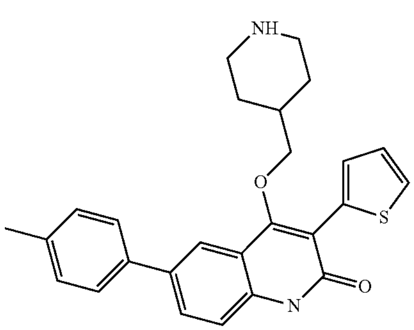 [SMILES: Cc1ccc(-c2ccc3[nH]c(=O)c(-c4cccs4)c(OCC4CCNCC4)c3c2)cc1] | 6-(4-methylphenyl)-4-(piperidin-4-ylmethoxy)-3-(thiophen-2-yl)quinolin-2(1H)-one | 430.56 |

| Cpd. | Structure | Name | Parent MW |
|---|---|---|---|
| 1-25 | 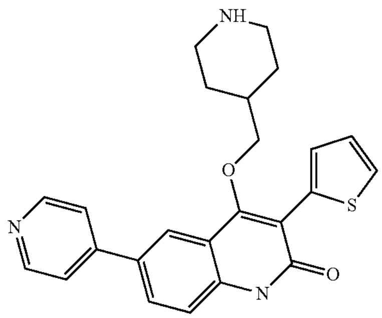 [SMILES: O=c1[nH]c2ccc(-c3ccncc3)cc2c(OCC2CCNCC2)c1-c1cccs1] | 4-(piperidin-4-ylmethoxy)-6-(pyridin-4-yl)-3-(thiophen-2-yl)quinolin-2(1H)-one | 417.52 |
| 1-26 | 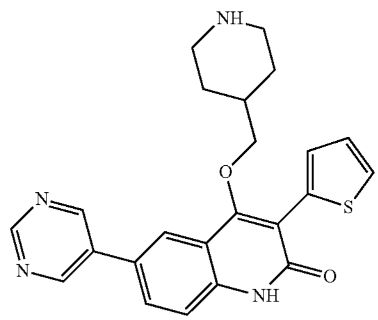 [SMILES: O=c1[nH]c2ccc(-c3cncnc3)cc2c(OCC2CCNCC2)c1-c1cccs1] | 4-(piperidin-4-ylmethoxy)-6-(pyrimidin-5-yl)-3-(thiophen-2-yl)quinolin-2(1H)-one | 418.51 |
| 1-27 | 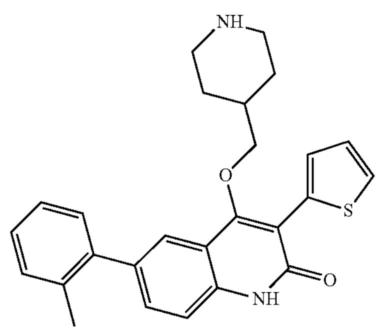 [SMILES: Cc1ccccc1-c1ccc2[nH]c(=O)c(-c3cccs3)c(OCC3CCNCC3)c2c1] | 6-(2-methylphenyl)-4-(piperidin-4-ylmethoxy)-3-(thiophen-2-yl)quinolin-2(1H)-one | 430.56 |
| 1-28 | 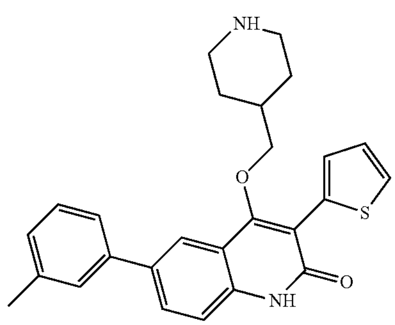 [SMILES: Cc1cccc(-c2ccc3[nH]c(=O)c(-c4cccs4)c(OCC4CCNCC4)c3c2)c1] | 6-(3-methylphenyl)-4-(piperidin-4-ylmethoxy)-3-(thiophen-2-yl)quinolin-2(1H)-one | 430.56 |
| 1-29 | 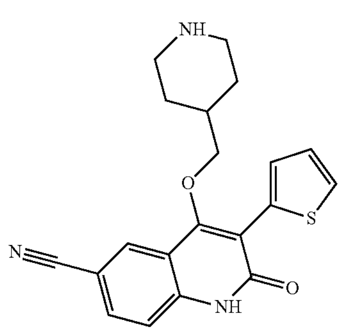 [SMILES: N#Cc1ccc2[nH]c(=O)c(-c3cccs3)c(OCC3CCNCC3)c2c1] | 2-oxo-4-(piperidin-4-ylmethoxy)-3-(thiophen-2-yl)-1,2-dihydroquinoline-6-carbonitrile | 365.45 |

-continued

| Cpd. | Structure | Name | Parent MW |
|---|---|---|---|
| 1-30 | 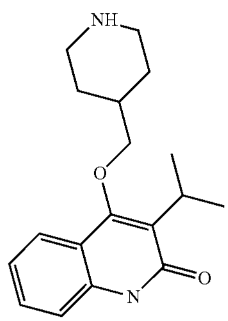 [SMILES: CC(C)c1c(OCC2CCNCC2)c2ccccc2[nH]c1=O] | 4-(piperidin-4-ylmethoxy)-3-(propan-2-yl)quinolin-2(1H)-one | 300.40 |
| 1-31 | 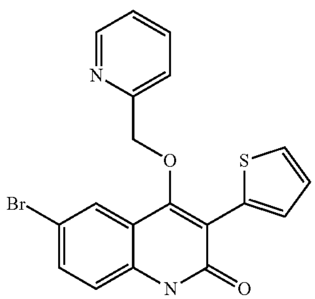 [SMILES: O=c1[nH]c2ccc(Br)cc2c(OCc2ccccn2)c1-c1cccs1] | 6-bromo-4-(pyridin-2-ylmethoxy)-3-(thiophen-2-yl)quinolin-2(1H)-one | 413.29 |
| 1-32 | 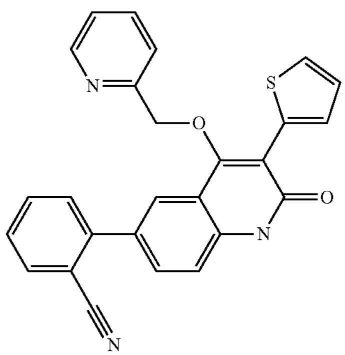 [SMILES: N#Cc1ccccc1-c1ccc2[nH]c(=O)c(-c3cccs3)c(OCc3ccccn3)c2c1] | 2-[2-oxo-4-(pyridin-2-ylmethoxy)-3-(thiophen-2-yl)-1,2-dihydroquinolin-6-yl]benzonitrile | 435.50 |
| 1-33 | 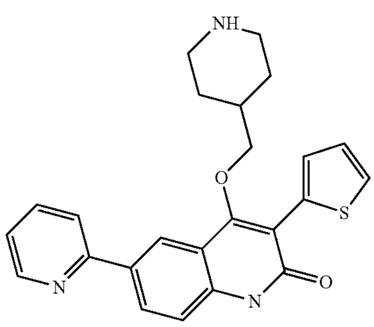 [SMILES: O=c1[nH]c2ccc(-c3ccccn3)cc2c(OCC2CCNCC2)c1-c1cccs1] | 4-(piperidin-4-ylmethoxy)-6-(pyridin-2-yl)-3-(thiophen-2-yl)quinolin-2(1H)-one | 417.52 |
| 1-34 | 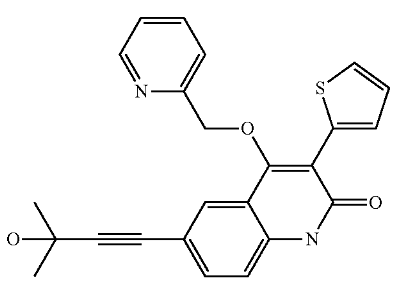 [SMILES: CC(C)(O)C#Cc1ccc2[nH]c(=O)c(-c3cccs3)c(OCc3ccccn3)c2c1] | 6-(3-hydroxy-3-methylbut-1-yn-1-yl)-4-(pyridin-2-ylmethoxy)-3-(thiophen-2-yl)quinolin-2(1H)-one | 416.49 |

-continued

| Cpd. | Structure | Name | Parent MW |
|---|---|---|---|
| 1-35 | 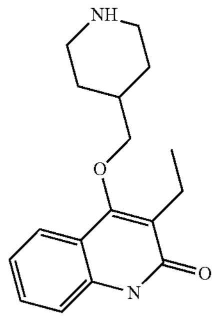 [SMILES: CCc1c(OCC2CCNCC2)c2ccccc2[nH]c1=O] | 3-ethyl-4-(piperidin-4-ylmethoxy)quinolin-2(1H)-one | 286.37 |
| 1-36 | 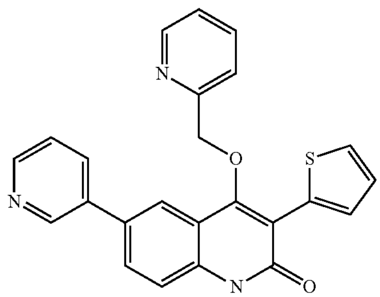 [SMILES: O=c1[nH]c2ccc(-c3cccnc3)cc2c(OCc2ccccn2)c1-c1cccs1] | 6-(pyridin-3-yl)-4-(pyridin-2-ylmethoxy)-3-(thiophen-2-yl)quinolin-2(1H)-one | 411.48 |
| 1-37 | 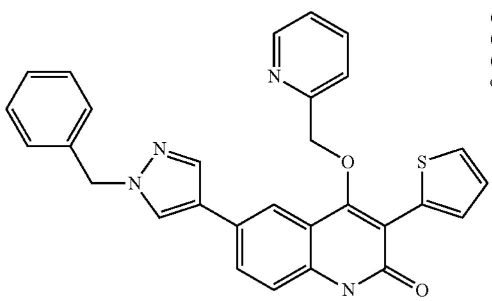 [SMILES: O=c1[nH]c2ccc(-c3cnn(Cc4ccccc4)c3)cc2c(OCc2ccccn2)c1-c1cccs1] | 6-(1-benzyl-1H-pyrazol-4-yl)-4-(pyridin-2-ylmethoxy)-3-(thiophen-2-yl)quinolin-2(1H)-one | 490.58 |
| 1-38 | 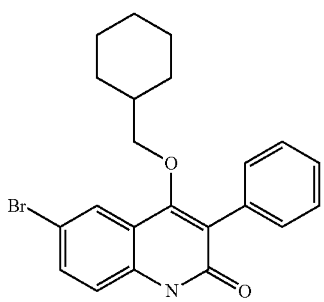 [SMILES: O=c1[nH]c2ccc(Br)cc2c(OCC2CCCCC2)c1-c1ccccc1] | 6-bromo-4-(cyclohexylmethoxy)-3-phenylquinolin-2(1H)-one | 412.32 |
| 1-39 | 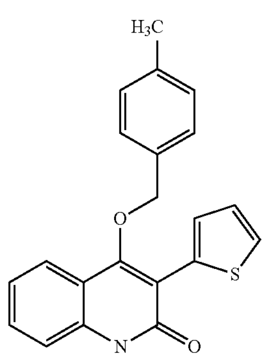 [SMILES: Cc1ccc(COc2c(-c3cccs3)c(=O)[nH]c3ccccc23)cc1] | 4-[(4-methylbenzyl)oxy]-3-(thiophen-2-yl)quinolin-2(1H)-one | 347.43 |

-continued
| Cpd. | Structure | Name | Parent MW |
|---|---|---|---|
| 1-40 | 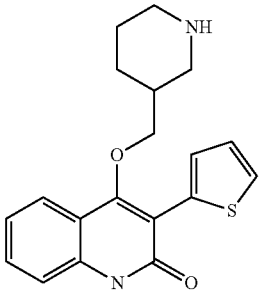 [SMILES: O=c1[nH]c2ccccc2c(OCC2CCCNC2)c1-c1cccs1] | 4-(piperidin-3-ylmethoxy)-3-(thiophen-2-yl)quinolin-2(1H)-one | 340.44 |
| 1-41 | 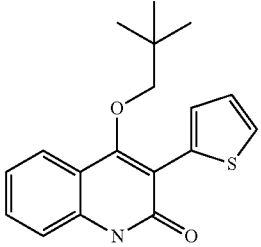 [SMILES: CC(C)(C)COc1c(-c2cccs2)c(=O)[nH]c2ccccc12] | 4-(2,2-dimethylpropoxy)-3-(thiophen-2-yl)quinolin-2(1H)-one | 313.41 |
| 1-42 | 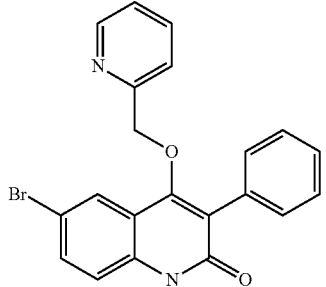 [SMILES: O=c1[nH]c2ccc(Br)cc2c(OCc2ccccn2)c1-c1ccccc1] | 6-bromo-3-phenyl-4-(pyridin-2-ylmethoxy)quinolin-2(1H)-one | 407.26 |
| 1-43 | 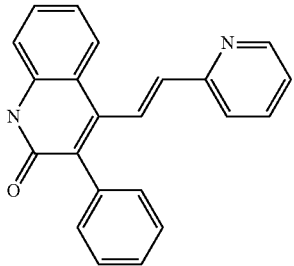 [SMILES: O=c1[nH]c2ccccc2c(/C=C/c2ccccn2)c1-c1ccccc1] | 3-phenyl-4-[(E)-2-(pyridin-2-yl)ethenyl]quinolin-2(1H)-one | 324.38 |
| 1-44 | 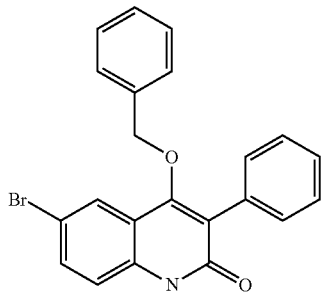 [SMILES: O=c1[nH]c2ccc(Br)cc2c(OCc2ccccc2)c1-c1ccccc1] | 4-(benzyloxy)-6-bromo-3-phenylquinolin-2(1H)-one | 406.27 |

-continued

| Cpd. | Structure | Name | Parent MW |
|---|---|---|---|
| 1-45 | 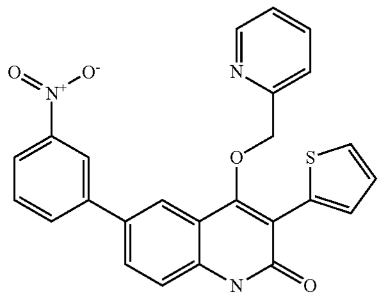 [SMILES: O=c1[nH]c2ccc(-c3cccc([N+](=O)[O-])c3)cc2c(OCc2ccccn2)c1-c1cccs1] | 6-(3-nitrophenyl)-4-(pyridin-2-ylmethoxy)-3-(thiophen-2-yl)quinolin-2(1H)-one | 455.49 |
| 1-46 | 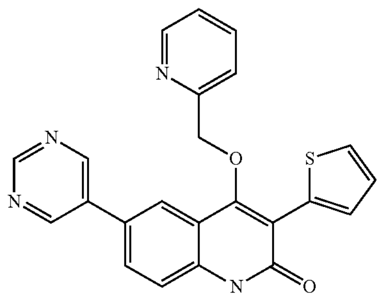 [SMILES: O=c1[nH]c2ccc(-c3cncnc3)cc2c(OCc2ccccn2)c1-c1cccs1] | 4-(pyridin-2-ylmethoxy)-6-(pyrimidin-5-yl)-3-(thiophen-2-yl)quinolin-2(1H)-one | 412.46 |
| 1-47 | 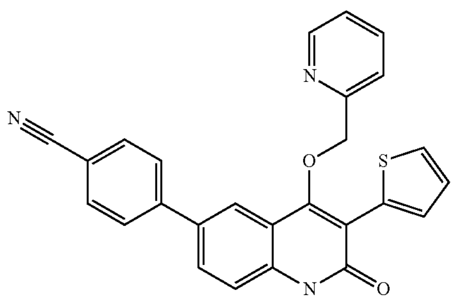 [SMILES: N#Cc1ccc(-c2ccc3[nH]c(=O)c(-c4cccs4)c(OCc4ccccn4)c3c2)cc1] | 4-[2-oxo-4-(pyridin-2-ylmethoxy)-3-(thiophen-2-yl)-1,2-dihydroquinolin-6-yl]benzonitrile | 435.50 |
| 1-48 | 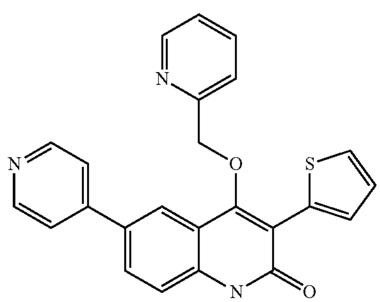 [SMILES: O=c1[nH]c2ccc(-c3ccncc3)cc2c(OCc2ccccn2)c1-c1cccs1] | 6-(pyridin-4-yl)-4-(pyridin-2-ylmethoxy)-3-(thiophen-2-yl)quinolin-2(1H)-one | 411.48 |
| 1-49 | 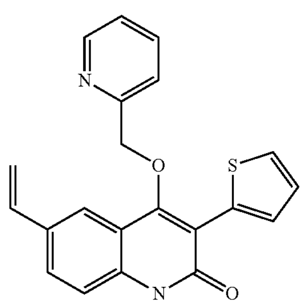 [SMILES: C=Cc1ccc2[nH]c(=O)c(-c3cccs3)c(OCc3ccccn3)c2c1] | 6-ethenyl-4-(pyridin-2-ylmethoxy)-3-(thiophen-2-yl)quinolin-2(1H)-one | 360.43 |

-continued

| Cpd. | Structure | Name | Parent MW |
|---|---|---|---|
| 1-50 | 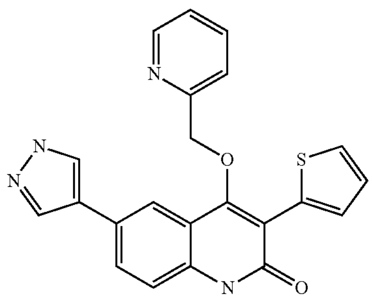 [SMILES: O=c1[nH]c2ccc(-c3cn[nH]c3)cc2c(OCc2ccccn2)c1-c1cccs1] | 6-(1H-pyrazol-4-yl)-4-(pyridin-2-ylmethoxy)-3-(thiophen-2-yl)quinolin-2(1H)-one | 400.45 |
| 1-51 | 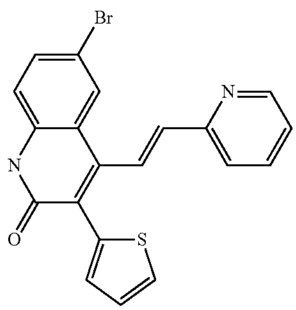 [SMILES: O=c1[nH]c2ccc(Br)cc2c(/C=C/c2ccccn2)c1-c1cccs1] | 6-bromo-4-[(E)-2-(pyridin-2-yl)ethenyl]-3-(thiophen-2-yl)quinolin-2(1H)-one | 409.30 |
| 1-52 | 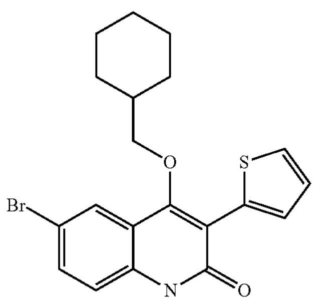 [SMILES: O=c1[nH]c2ccc(Br)cc2c(OCC2CCCCC2)c1-c1cccs1] | 6-bromo-4-(cyclohexylmethoxy)-3-(thiophen-2-yl)quinolin-2(1H)-one | 418.35 |
| 1-53 | 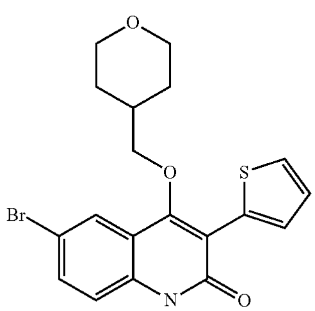 [SMILES: O=c1[nH]c2ccc(Br)cc2c(OCC2CCOCC2)c1-c1cccs1] | 6-bromo-4-(tetrahydro-2H-pyran-4-ylmethoxy)-3-(thiophen-2-yl)quinolin-2(1H)-one | 420.32 |
| 1-54 | 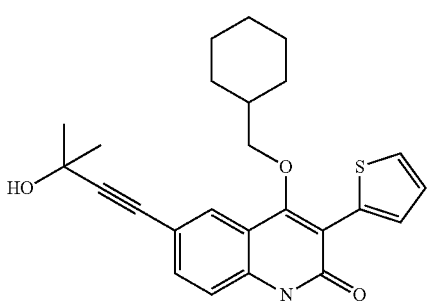 [SMILES: CC(C)(O)C#Cc1ccc2[nH]c(=O)c(-c3cccs3)c(OCC3CCCCC3)c2c1] | 4-(cyclohexylmethoxy)-6-(3-hydroxy-3-methylbut-1-yn-1-yl)-3-(thiophen-2-yl)quinolin-2(1H)-one | 421.55 |

-continued

| Cpd. | Structure | Name | Parent MW |
|---|---|---|---|
| 1-55 | 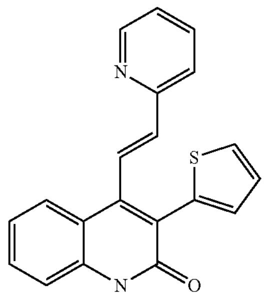 [SMILES: O=c1[nH]c2ccccc2c(/C=C/c2ccccn2)c1-c1cccs1] | 4-[(E)-2-(pyridin-2-yl)ethenyl]-3-(thiophen-2-yl)quinolin-2(1H)-one | 330.40 |
| 1-56 | 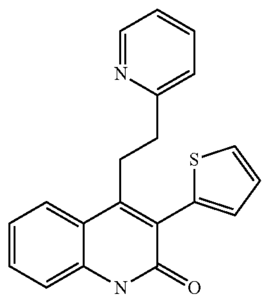 [SMILES: O=c1[nH]c2ccccc2c(CCc2ccccn2)c1-c1cccs1] | 4-[2-(pyridin-2-yl)ethyl]-3-(thiophen-2-yl)quinolin-2(1H)-one | 332.42 |
| 1-57 | 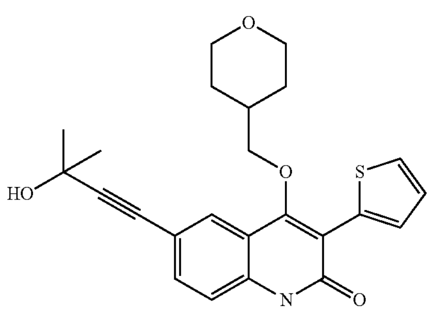 [SMILES: CC(C)(O)C#Cc1ccc2[nH]c(=O)c(-c3cccs3)c(OCC3CCOCC3)c2c1] | 6-(3-hydroxy-3-methylbut-1-yn-1-yl)-4-(tetrahydro-2H-pyran-4-ylmethoxy)-3-(thiophen-2-yl)quinolin-2(1H)-one | 423.52 |
| 1-58 | 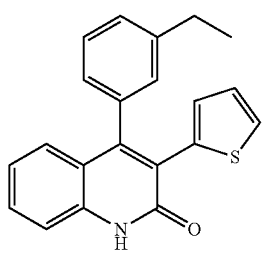 [SMILES: CCc1cccc(-c2c(-c3cccs3)c(=O)[nH]c3ccccc23)c1] | 4-(3-ethylphenyl)-3-(thiophen-2-yl)quinolin-2(1H)-one | 331.41 |
| 1-59 | 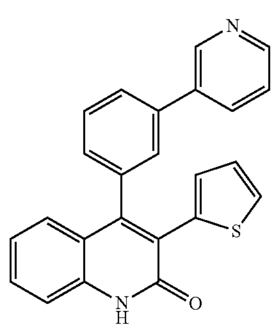 [SMILES: O=c1[nH]c2ccccc2c(-c2cccc(-c3cccnc3)c2)c1-c1cccs1] | 4-[3-(pyridin-3-yl)phenyl]-3-(thiophen-2-yl)quinolin-2(1H)-one | 380.46 |

-continued

| Cpd. | Structure | Name | Parent MW |
|---|---|---|---|
| 1-60 | 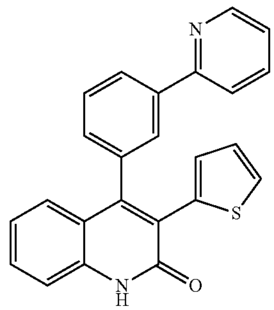 [SMILES: O=c1[nH]c2ccccc2c(-c2cccc(-c3ccccn3)c2)c1-c1cccs1] | 4-[3-(pyridin-2-yl)phenyl]-3-(thiophen-2-yl)quinolin-2(1H)-one | 380.46 |
| 1-61 | 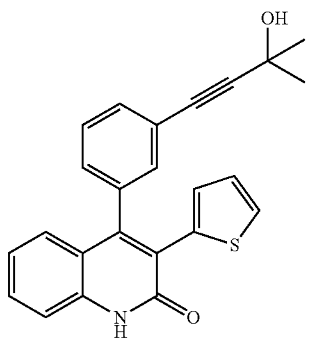 [SMILES: CC(C)(O)C#Cc1cccc(-c2c(-c3cccs3)c(=O)[nH]c3ccccc23)c1] | 4-[3-(3-hydroxy-3-methylbut-1-yn-1-yl)phenyl]-3-(thiophen-2-yl)quinolin-2(1H)-one | 385.48 |
| 1-62 | 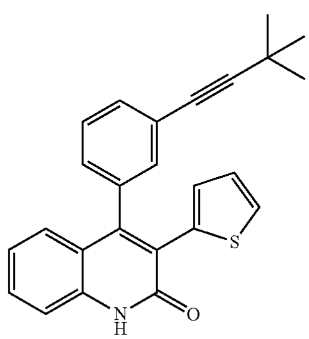 [SMILES: CC(C)(C)C#Cc1cccc(-c2c(-c3cccs3)c(=O)[nH]c3ccccc23)c1] | 4-[3-(3,3-dimethylbut-1-yn-1-yl)phenyl]-3-(thiophen-2-yl)quinolin-2(1H)-one | 383.51 |
| 1-63 | 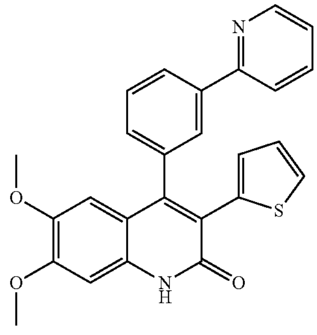 | 6,7-dimethoxy-4-[3-(pyridin-2-yl)phenyl]-3-(thiophen-2-yl)quinolin-2(1H)-one | 440.51 |

-continued

| Cpd. | Structure | Name | Parent MW |
|---|---|---|---|
| 1-64 | 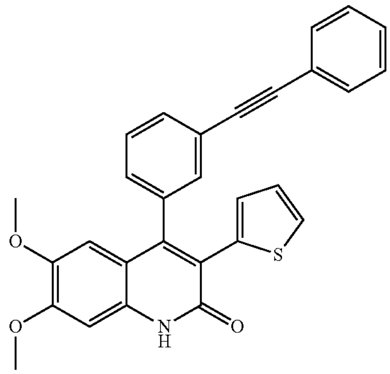 [SMILES: COc1cc2[nH]c(=O)c(-c3cccs3)c(-c3cccc(C#Cc4ccccc4)c3)c2cc1OC] | 6,7-dimethoxy-4-[3-(phenylethynyl)phenyl]-3-(thiophen-2-yl)quinolin-2(1H)-one | 463.55 |
| 1-65 | 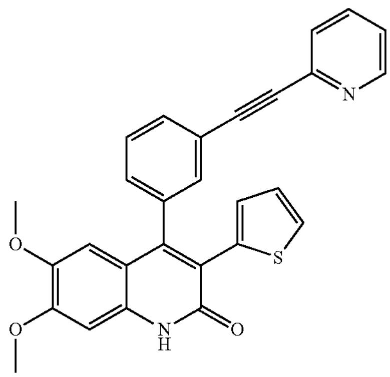 [SMILES: COc1cc2[nH]c(=O)c(-c3cccs3)c(-c3cccc(C#Cc4ccccn4)c3)c2cc1OC] | 6,7-dimethoxy-4-[3-(pyridin-2-ylethynyl)phenyl]-3-(thiophen-2-yl)quinolin-2(1H)-one | 464.53 |
| 1-66 | 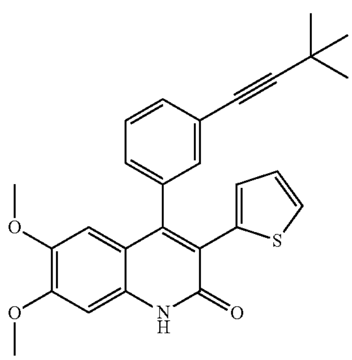 [SMILES: COc1cc2[nH]c(=O)c(-c3cccs3)c(-c3cccc(C#CC(C)(C)C)c3)c2cc1OC] | 4-[3-(3,3-dimethylbut-1-yn-1-yl)phenyl]-6,7-dimethoxy-3-(thiophen-2-yl)quinolin-2(1H)-one | 443.56 |
| 1-67 | 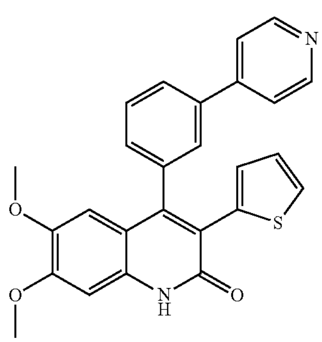 [SMILES: COc1cc2[nH]c(=O)c(-c3cccs3)c(-c3cccc(-c4ccncc4)c3)c2cc1OC] | 6,7-dimethoxy-4-[3-(pyridin-4-yl)phenyl]-3-(thiophen-2-yl)quinolin-2(1H)-one | 440.51 |

-continued

| Cpd. | Structure | Name | Parent MW |
|---|---|---|---|
| 1-68 | 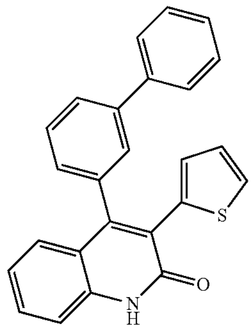 [SMILES: O=c1[nH]c2ccccc2c(-c2cccc(-c3ccccc3)c2)c1-c1cccs1] | 4-(biphenyl-3-yl)-3-(thiophen-2-yl)quinolin-2(1H)-one | 379.47 |
| 1-69 | 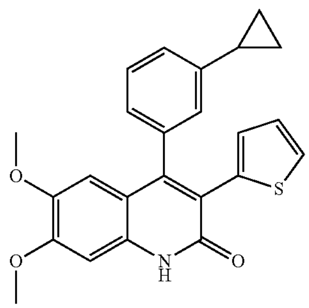 [SMILES: COc1cc2[nH]c(=O)c(-c3cccs3)c(-c3cccc(C4CC4)c3)c2cc1OC] | 4-(3-cyclopropylphenyl)-6,7-dimethoxy-3-(thiophen-2-yl)quinolin-2(1H)-one | 403.49 |
| 1-70 | 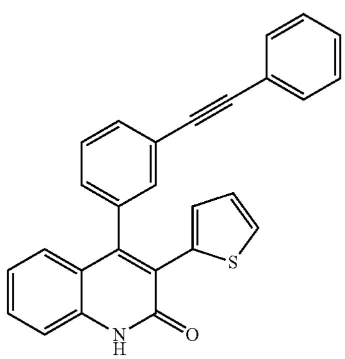 [SMILES: O=c1[nH]c2ccccc2c(-c2cccc(C#Cc3ccccc3)c2)c1-c1cccs1] | 4-[3-(phenylethynyl)phenyl]-3-(thiophen-2-yl)quinolin-2(1H)-one | 403.49 |
| 1-71 | 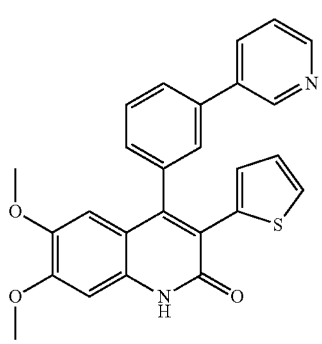 [SMILES: COc1cc2[nH]c(=O)c(-c3cccs3)c(-c3cccc(-c4cccnc4)c3)c2cc1OC] | 6,7-dimethoxy-4-[3-(pyridin-3-yl)phenyl]-3-(thiophen-2-yl)quinolin-2(1H)-one | 440.51 |

-continued

| Cpd. | Structure | Name | Parent MW |
|---|---|---|---|
| 1-72 | 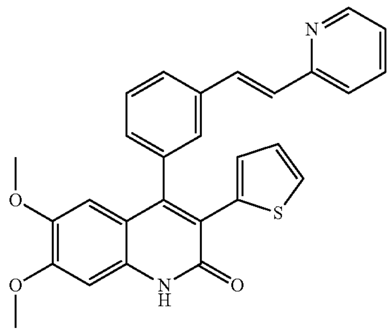 [SMILES: COc1cc2[nH]c(=O)c(-c3cccs3)c(-c3cccc(/C=C/c4ccccn4)c3)c2cc1OC] | 6,7-dimethoxy-4-{3-[(E)-2-(pyridin-2-yl)ethenyl]phenyl}-3-(thiophen-2-yl)quinolin-2(1H)-one | 466.55 |
| 1-73 | 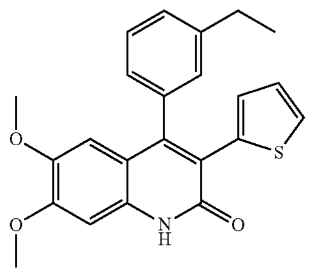 [SMILES: CCc1cccc(-c2c(-c3cccs3)c(=O)[nH]c3cc(OC)c(OC)cc23)c1] | 4-(3-ethylphenyl)-6,7-dimethoxy-3-(thiophen-2-yl)quinolin-2(1H)-one | 391.48 |
| 1-74 | 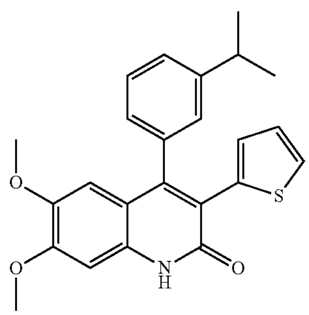 [SMILES: COc1cc2[nH]c(=O)c(-c3cccs3)c(-c3cccc(C(C)C)c3)c2cc1OC] | 6,7-dimethoxy-4-[3-(propan-2-yl)phenyl]-3-(thiophen-2-yl)quinolin-2(1H)-one | 405.51 |
| 1-75 | 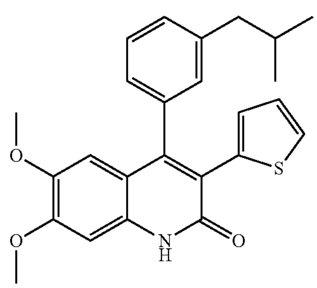 [SMILES: COc1cc2[nH]c(=O)c(-c3cccs3)c(-c3cccc(CC(C)C)c3)c2cc1OC] | 6,7-dimethoxy-4-[3-(2-methylpropyl)phenyl]-3-(thiophen-2-yl)quinolin-2(1H)-one | 419.54 |
| 1-76 | 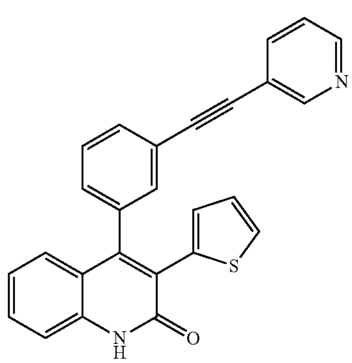 [SMILES: O=c1[nH]c2ccccc2c(-c2cccc(C#Cc3cccnc3)c2)c1-c1cccs1] | 4-[3-(pyridin-3-ylethynyl)phenyl]-3-(thiophen-2-yl)quinolin-2(1H)-one | 404.48 |

| Cpd. | Structure | Name | Parent MW |
|---|---|---|---|
| 1-77 | 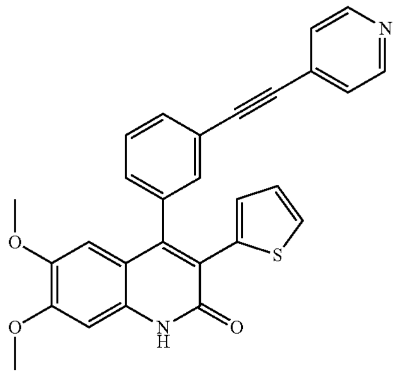 [SMILES: COc1cc2[nH]c(=O)c(-c3cccs3)c(-c3cccc(C#Cc4ccncc4)c3)c2cc1OC] | 6,7-dimethoxy-4-[3-(pyridin-4-ylethynyl)phenyl]-3-(thiophen-2-yl)quinolin-2(1H)-one | 464.53 |
| 1-78 | 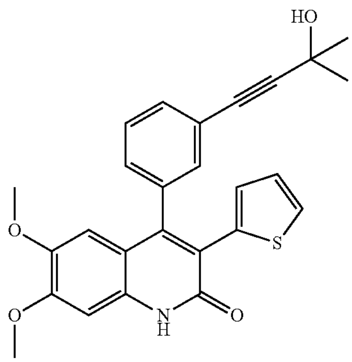 [SMILES: COc1cc2[nH]c(=O)c(-c3cccs3)c(-c3cccc(C#CC(C)(C)O)c3)c2cc1OC] | 4-[3-(3-hydroxy-3-methylbut-1-yn-1-yl)phenyl]-6,7-dimethoxy-3-(thiophen-2-yl)quinolin-2(1H)-one | 445.53 |
| 1-79 | 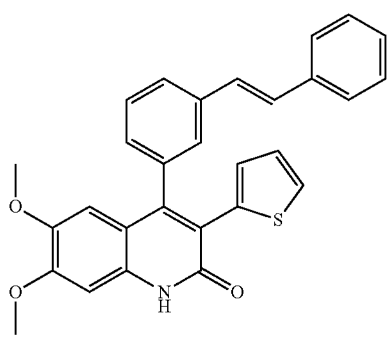 [SMILES: COc1cc2[nH]c(=O)c(-c3cccs3)c(-c3cccc(/C=C/c4ccccc4)c3)c2cc1OC] | 6,7-dimethoxy-4-{3-[(E)-2-phenylethenyl]phenyl}-3-(thiophen-2-yl)quinolin-2(1H)-one | 465.56 |
| 1-80 | 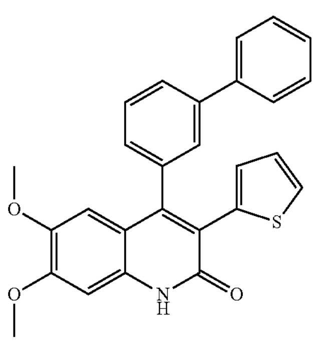 [SMILES: COc1cc2[nH]c(=O)c(-c3cccs3)c(-c3cccc(-c4ccccc4)c3)c2cc1OC] | 4-(biphenyl-3-yl)-6,7-dimethoxy-3-(thiophen-2-yl)quinolin-2(1H)-one | 439.53 |

| Cpd. | Structure | Name | Parent MW |
|---|---|---|---|
| 1-81 | 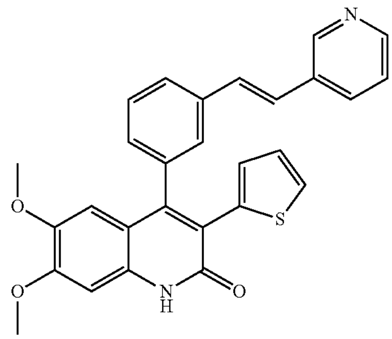 [SMILES: COc1cc2[nH]c(=O)c(-c3cccs3)c(-c3cccc(/C=C/c4cccnc4)c3)c2cc1OC] | 6,7-dimethoxy-4-{3-[(E)-2-(pyridin-3-yl)ethenyl]phenyl}-3-(thiophen-2-yl)quinolin-2(1H)-one | 466.55 |
| 1-82 | 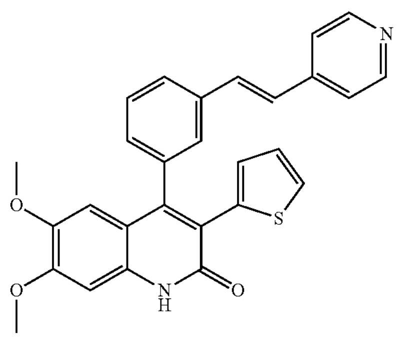 [SMILES: COc1cc2[nH]c(=O)c(-c3cccs3)c(-c3cccc(/C=C/c4ccncc4)c3)c2cc1OC] | 6,7-dimethoxy-4-{3-[(E)-2-(pyridin-4-yl)ethenyl]phenyl}-3-(thiophen-2-yl)quinolin-2(1H)-one | 466.55 |
| 1-83 | 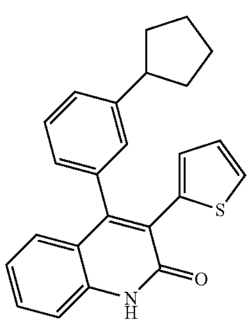 [SMILES: O=c1[nH]c2ccccc2c(-c2cccc(C3CCCC3)c2)c1-c1cccs1] | 4-(3-cyclopentylphenyl)-3-(thiophen-2-yl)quinolin-2(1H)-one | 371.49 |
| 1-84 | 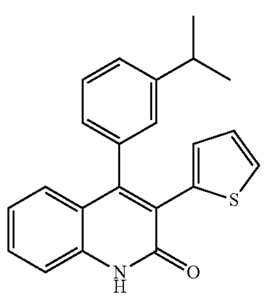 [SMILES: CC(C)c1cccc(-c2c(-c3cccs3)c(=O)[nH]c3ccccc23)c1] | 4-[3-(propan-2-yl)phenyl]-3-(thiophen-2-yl)quinolin-2(1H)-one | 345.46 |
| 1-85 | 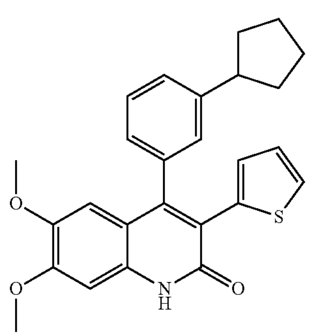 [SMILES: COc1cc2[nH]c(=O)c(-c3cccs3)c(-c3cccc(C4CCCC4)c3)c2cc1OC] | 4-(3-cyclopentylphenyl)-6,7-dimethoxy-3-(thiophen-2-yl)quinolin-2(1H)-one | 431.55 |

-continued

| Cpd. | Structure | Name | Parent MW |
|---|---|---|---|
| 1-86 | 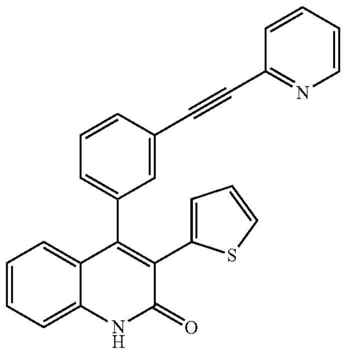 [SMILES: O=c1[nH]c2ccccc2c(-c2cccc(C#Cc3ccccn3)c2)c1-c1cccs1] | 4-[3-(pyridin-2-ylethynyl)phenyl]-3-(thiophen-2-yl)quinolin-2(1H)-one | 404.48 |
| 1-87 | 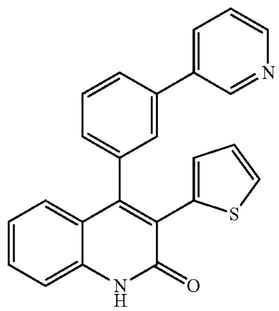 [SMILES: O=c1[nH]c2ccccc2c(-c2cccc(-c3cccnc3)c2)c1-c1cccs1] | 4-[3-(pyridin-3-yl)phenyl]-3-(thiophen-2-yl)quinolin-2(1H)-one | 380.46 |
| 1-88 | 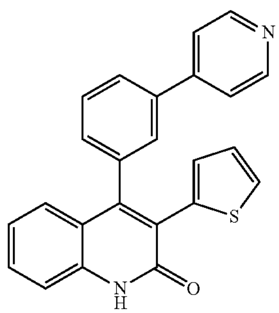 [SMILES: O=c1[nH]c2ccccc2c(-c2cccc(-c3ccncc3)c2)c1-c1cccs1] | 4-[3-(pyridin-4-yl)phenyl]-3-(thiophen-2-yl)quinolin-2(1H)-one | 380.46 |
| 1-89 | 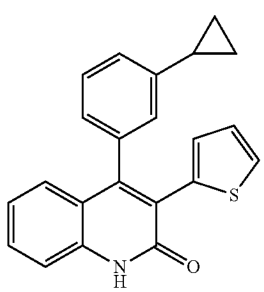 [SMILES: O=c1[nH]c2ccccc2c(-c2cccc(C3CC3)c2)c1-c1cccs1] | 4-(3-cyclopropylphenyl)-3-(thiophen-2-yl)quinolin-2(1H)-one | 343.44 |
| 1-90 | 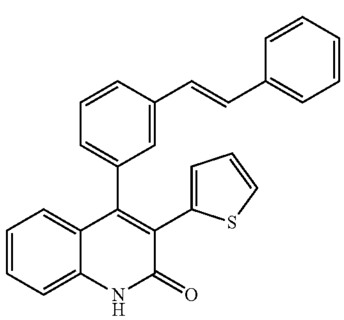 [SMILES: O=c1[nH]c2ccccc2c(-c2cccc(/C=C/c3ccccc3)c2)c1-c1cccs1] | 4-{3-[(E)-2-phenylethenyl]phenyl}-3-(thiophen-2-yl)quinolin-2(1H)-one | 405.51 |

-continued

| Cpd. | Structure | Name | Parent MW |
|---|---|---|---|
| 1-91 | 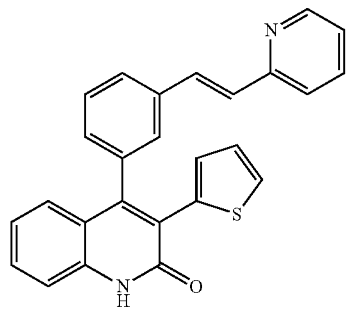 [SMILES: O=c1[nH]c2ccccc2c(-c2cccc(/C=C/c3ccccn3)c2)c1-c1cccs1] | 4-{3-[(E)-2-(pyridin-2-yl)ethenyl]phenyl}-3-(thiophen-2-yl)quinolin-2(1H)-one | 406.50 |
| 1-92 | 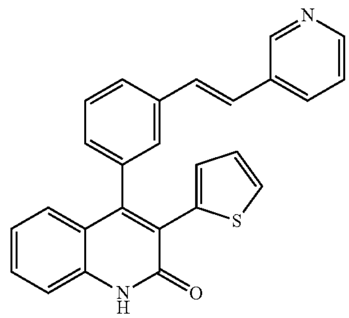 [SMILES: O=c1[nH]c2ccccc2c(-c2cccc(/C=C/c3cccnc3)c2)c1-c1cccs1] | 4-{3-[(E)-2-(pyridin-3-yl)ethenyl]phenyl}-3-(thiophen-2-yl)quinolin-2(1H)-one | 406.50 |
| 1-93 | 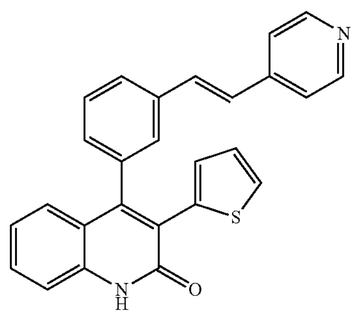 [SMILES: O=c1[nH]c2ccccc2c(-c2cccc(/C=C/c3ccncc3)c2)c1-c1cccs1] | 4-{3-[(E)-2-(pyridin-4-yl)ethenyl]phenyl}-3-(thiophen-2-yl)quinolin-2(1H)-one | 406.50 |

Table 2

The following table shows representative data for the compounds of the Examples as PDE2 inhibitors as determined by the foregoing assays. In this table, the PDE2 Ki is a measure of the ability of the test compound to inhibit the action of the PDE2 enzyme.

| Compound | Structure | PDE2 Ki (nM) |
|---|---|---|
| 1-13 | 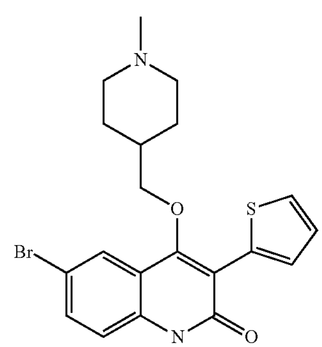 [SMILES: CN1CCC(COc2c(-c3cccs3)c(=O)[nH]c3ccc(Br)cc23)CC1] | 73 nM |

-continued

| Compound | Structure | PDE2 Ki (nM) |
|---|---|---|
| 1-15 | 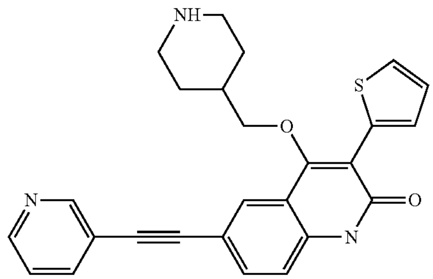 [SMILES: O=c1[nH]c2ccc(C#Cc3cccnc3)cc2c(OCC2CCNCC2)c1-c1cccs1] | 1.3 nM |
| 1-18 | 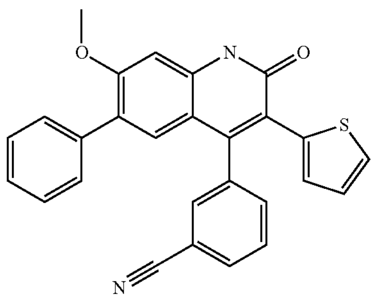 [SMILES: COc1cc2[nH]c(=O)c(-c3cccs3)c(-c3cccc(C#N)c3)c2cc1-c1ccccc1] | 200 nM |
| 1-23 | 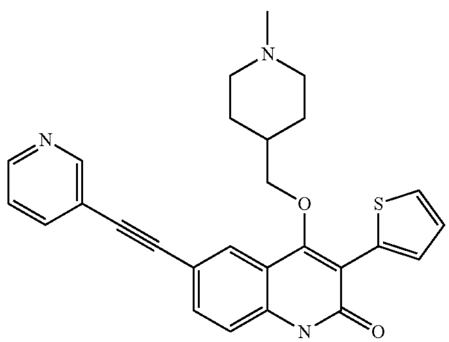 [SMILES: CN1CCC(COc2c(-c3cccs3)c(=O)[nH]c3ccc(C#Cc4cccnc4)cc23)CC1] | 62 nM |
| 1-48 | 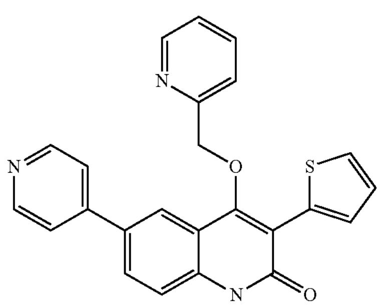 [SMILES: O=c1[nH]c2ccc(-c3ccncc3)cc2c(OCc2ccccn2)c1-c1cccs1] | 160 nM |
| 1-51 | 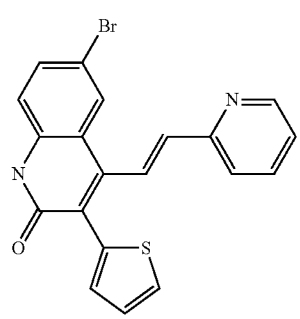 [SMILES: O=c1[nH]c2ccc(Br)cc2c(/C=C/c2ccccn2)c1-c1cccs1] | 900 nM |

-continued

| Compound | Structure | PDE2 Ki (nM) |
|---|---|---|
| 1-57 | 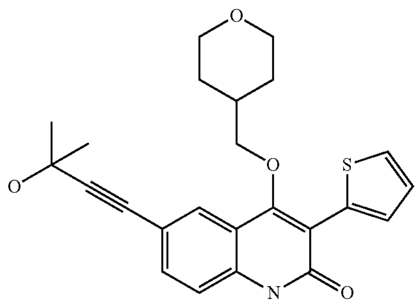 [SMILES: CC(C)(O)C#Cc1ccc2[nH]c(=O)c(-c3cccs3)c(OCC3CCOCC3)c2c1] | 1.8 nM |
| 1-63 | 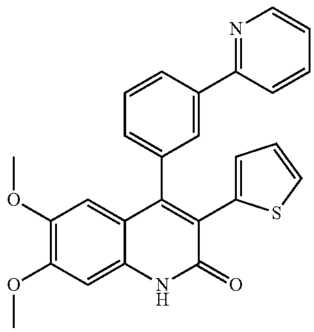 [SMILES: COc1cc2[nH]c(=O)c(-c3cccs3)c(-c3cccc(-c4ccccn4)c3)c2cc1OC] | 34 nM |
| 1-85 | 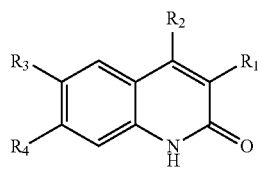 | 110 nM |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

I wherein:
$R_1$ is selected from the group consisting of:
(1) —$C_{5-6}$ heterocycle selected from the group consisting of thiophenyl and pyridyl, which is unsubstituted or substituted with $R_{14}$, provided that when $R_1$ is thiophenyl and $R_2$ is —O(CH$_2$)$_n$C$_{5-10}$ heterocycle then n is 0-1; and when $R_1$ is thiophenyl and $R_2$ is —OCH$_3$ then $R_3$ and $R_4$ are not both hydrogen;
(2) phenyl, which is unsubstituted;
(3) —$C_{1-6}$alkyl, which is unsubstituted or substituted with $R_{14}$;

$R_2$ is selected from the group consisting of:
(1) —O(C$_{1-6}$ alkyl), unsubstituted or substituted with $R_{14}$;
(2) —O(CH$_2$)$_n$C$_{6-10}$ aryl, which is unsubstituted or substituted with $R_{14}$;
(3) —O(CH$_2$)$_n$C$_{3-10}$ cycloakyl;
(4) —O(CH$_2$)$_n$C$_{5-10}$ heterocycle, which is unsubstituted or substituted with $R_{14}$,
(5) phenyl, substituted with $R_{14}$;
(6) —(CH$_2$)$_n$C$_{5-10}$ heterocycle, which is unsubstituted or substituted with $R_{14}$, provided said heterocycle is not thiophenyl;
(7) —(CH$_2$)$_n$C$_{5-10}$ aryl, which is unsubstituted or substituted with $R_{14}$;
(8) —(CH$_2$)$_n$C$_{3-10}$ cycloakyl;
(9) —(C$_{2-6}$ alkenyl)C$_{5-10}$ heterocycle, which is unsubstituted or substituted with $R_{14}$;

(10) —($C_{2-6}$ alkenyl)$C_{6-10}$ aryl, which is unsubstituted or substituted with $R_{14}$;
(11) —($C_{2-6}$ alkenyl)$C_{3-10}$ cycloalkyl, which is unsubstituted or substituted with $R_{14}$;
$R_3$ is selected from the group consisting of:
(1) Hydrogen
(2) Halogen
(3) —$C_{6-10}$aryl, which is unsubstituted or substituted with $R_{14}$;
(4) —$C_{5-10}$heteroaryl, which is unsubstituted or substituted with $R_{14}$;
(5) -(Q)$C_{6-10}$aryl, which is unsubstituted or substituted with $R_{14}$;
(6) -(Q)$C_{5-10}$heteroaryl, which is unsubstituted or substituted with $R_{14}$;
(7) -(Q)-C($R_5$,$R_6$)—OH;
(8) —CN;
(9) —$C_{2-4}$ alkenyl;
(10) —$OC_{1-6}$ alkyl;
Q is selected independently from:
a. —$C_{1-6}$ alkyl;
b. —$C_{2-4}$ alkynyl;
c. —$C_{2-4}$ alkenyl;
$R_4$, is selected independently from
(1) Hydrogen;
(2) —$(CH_2)_nCH_3$;
(3) —$OC_{1-6}$ alkyl;
(4) Halogen
$R_5$ and $R_6$ are selected independently from
(1) Hydrogen;
(2) —$(CH_2)_nCH_3$;
(3) —$OC_{1-6}$ alkyl;
$R_{14}$ is selected from the group consisting of:
(1) Hydroxyl;
(2) Halogen;
(3) $C_{1-6}$alkyl;
(4) —CN;
(5) —$CO_2H$;
(6) —C(O)$NH_2$;
(7) —$(CH_2)_nC_{6-10}$aryl;
(8) —$(CH_2)_nC_{5-10}$heterocycle;
(9) —$NO_2$;
(10) -(Q)-C($R_5$,$R_6$)—OH;
(11) -Q$(CH_2)_nC_{6-10}$heteroaryl, which is unsubstituted or substituted with $R_{15}$;
(12) —$(CH_2)_nC_{3-10}$cycloakyl;
(13) -Q$(CH_2)_nC_{6-10}$aryl, which is unsubstituted or substituted with $R_{15}$;
$R^{15}$ is selected from the group consisting of:
(1) Hydroxyl;
(2) Halogen;
(3) $C_{1-6}$alkyl;
(4) —CN; and
n is 0-3;
or a pharmaceutically acceptable salt thereof.

2. The compound of claim 1 wherein $R_1$ is thiophenyl, which is unsubstituted or substituted with $R_{14}$, provided that when $R_1$ is thiophenyl and $R_2$ is —O$(CH_2)_nC_{5-10}$ heterocycle then n is 0-1 and when $R_1$ is thiophenyl and $R_2$ is —$OCH_3$ then R3 and R4 are not both hydrogen.

3. The compound of claim 2 wherein n is 1.

4. The compound of claim 1 wherein $R_1$ is pyridyl.

5. The compound of claim 1 wherein $R_1$ is unsubstituted phenyl.

6. The compound of claim 1 wherein $R_2$ is selected from the group consisting of —O(CH2)$_n C_{6-10}$aryl, —O$(CH_2)_nC_{3-10}$cycloalkyl, —O$(CH2)_nC_{5-10}$heterocycle, substituted phenyl and —($C_{2-6}$ alkenyl)$C_{5-10}$heterocycle, said aryl, cycloalkyl, and heterocycle unsubstituted or substituted with $R_{14}$.

7. The compound according to claim 6 wherein the cycloalkyl, and heterocycle is optionally substituted pyranyl, pyridyl, piperidinyl, or cyclohexyl, said alkenyl is ethylenyl, and n is 0-1.

8. The compound according to claim 1 wherein $R_3$ is selected from the group consisting of hydrogen, halogen, —$C_{6-10}$aryl, —$C_{5-10}$heteroaryl, and -(Q)-C($R_5$,$R_6$)—OH, said aryl and heteroaryl unsubstituted or substituted with $R_{14}$.

9. The compound according to claim 8 wherein $R_3$ is hydrogen, bromine, iodine, phenyl, pyridyl, pyrazolyl, pyrimidinyl, and -(Q)-C($R_5$,$R_6$)—OH, wherein $R_5$ and $R_6$ are $C_{1-6}$ alky, and Q is $C_2$alkynyl, and wherein said phenyl, pyridyl, pyrazolyl and pyrimidinyl are optionally substituted with 1 to 3 groups of $R_{14}$.

10. The compound according to claim 1 wherein $R_1$ is thiophenyl, $R_2$ is optionally substituted O(CH2)$_n$pyranyl, O(CH2)$_n$pyridyl, O(CH2)$_n$piperidinyl, O(CH2)$_n$phenyl, O(CH2)$_n$cyclohexyl, and —($C_{2-6}$ alkenyl)$C_{5-10}$heterocycle, wherein said alkenyl is ethylenyl, and n is 0-1.

11. A compound which is selected from the group consisting of:
6-phenyl-4-(pyridin-2-ylmethoxy)-3-(thiophen-2-yl)quinolin-2(1H)-one;
6-iodo-4-(pyridin-4-ylmethoxy)-3-(thiophen-2-yl)quinolin-2(1H)-one;
4-[(3-methylbenzyl)oxy]-3-(thiophen-2-yl)quinolin-2(1H)-one;
4-(cyclohexylmethoxy)-3-(thiophen-2-yl)quinolin-2(1H)-one;
4-(pyridin-4-ylmethoxy)-3-(thiophen-2-yl)quinolin-2(1H)-one;
4-(pyridin-3-yl)-3-(thiophen-2-yl)quinolin-2(1H)-one;
4-(piperidin-4-ylmethoxy)-3-(pyridin-3-yl)quinolin-2(1H)-one;
4-(benzyloxy)-3-(thiophen-2-yl)quinolin-2(1H)-one;
3-(6-bromo-7-methoxy-2-oxo-3-phenyl-1,2-dihydroquinolin-4-yl)benzonitrile;
3-[6-bromo-7-methoxy-2-oxo-3-(thiophen-2-yl)-1,2-dihydroquinolin-4-yl]benzonitrile;
6-phenyl-4-(piperidin-4-ylmethoxy)-3-(thiophen-2-yl)quinolin-2(1H)-one;
3-(6-bromo-7-methoxy-2-oxo-3-phenyl-1,2-dihydroquinolin-4-yl)benzamide;
6-bromo-4-[(1-methylpiperidin-4-yl)methoxy]-3-(thiophen-2-yl)quinolin-2(1H)-one;
4-(piperidin-4-ylmethoxy)-6-(pyridin-3-yl)-3-(thiophen-2-yl)quinolin-2(1H)-one;
4-(piperidin-4-ylmethoxy)-6-(pyridin-3-ylethynyl)-3-(thiophen-2-yl)quinolin-2(1H)-one;
6-(phenylethynyl)-4-(piperidin-4-ylmethoxy)-3-(thiophen-2-yl)quinolin-2(1H)-one;
2-[2-oxo-4-(piperidin-4-ylmethoxy)-3-(thiophen-2-yl)-1,2-dihydroquinolin-6-yl]benzonitrile;
3-[7-methoxy-2-oxo-6-phenyl-3-(thiophen-2-yl)-1,2-dihydroquinolin-4-yl]benzonitrile;
4-(piperidin-4-ylmethoxy)-3-(thiophen-2-yl)quinolin-2(1H)-one;
4-(piperidin-4-ylmethoxy)-3-(pyridin-4-yl)quinolin-2(1H)-one;
3-methyl-4-(piperidin-4-ylmethoxy)quinolin-2(1H)-one;
4-(piperidin-4-ylmethoxy)-6-(pyridin-3-yl)-3-(thiophen-2-yl)quinolin-2(1H)-one;
4-[(1-methylpiperidin-4-yl)methoxy]-6-(pyridin-3-ylethynyl)-3-(thiophen-2-yl)quinolin-2(1H)-one;

6-(4-methylphenyl)-4-(piperidin-4-ylmethoxy)-3-(thiophen-2-yl)quinolin-2(1H)-one;
4-(piperidin-4-ylmethoxy)-6-(pyridin-4-yl)-3-(thiophen-2-yl)quinolin-2(1H)-one;
4-(piperidin-4-ylmethoxy)-6-(pyrimidin-5-yl)-3-(thiophen-2-yl)quinolin-2(1H)-one;
6-(2-methylphenyl)-4-(piperidin-4-ylmethoxy)-3-(thiophen-2-yl)quinolin-2(1H)-one;
6-(3-methylphenyl)-4-(piperidin-4-ylmethoxy)-3-(thiophen-2-yl)quinolin-2(1H)-one;
2-oxo-4-(piperidin-4-ylmethoxy)-3-(thiophen-2-yl)-1,2-dihydroquinoline-6-carbonitrile;
4-(piperidin-4-ylmethoxy)-3-(propan-2-yl)quinolin-2(1H)-one;
6-bromo-4-(pyridin-2-ylmethoxy)-3-(thiophen-2-yl)quinolin-2(1H)-one;
2-[2-oxo-4-(pyridin-2-ylmethoxy)-3-(thiophen-2-yl)-1,2-dihydroquinolin-6-yl]benzonitrile;
4-(piperidin-4-ylmethoxy)-6-(pyridin-2-yl)-3-(thiophen-2-yl)quinolin-2(1H)-one;
6-(3-hydroxy-3-methylbut-1-yn-1-yl)-4-(pyridin-2-ylmethoxy)-3-(thiophen-2-yl)quinolin-2(1H)-one;
3-ethyl-4-(piperidin-4-ylmethoxy)quinolin-2(1H)-one;
6-(pyridin-3-yl)-4-(pyridin-2-ylmethoxy)-3-(thiophen-2-yl)quinolin-2(1H)-one;
6-(1-benzyl-1H-pyrazol-4-yl)-4-(pyridin-2-ylmethoxy)-3-(thiophen-2-yl)quinolin-2(1H)-one;
6-bromo-4-(cyclohexylmethoxy)-3-phenylquinolin-2(1H)-one;
4-[(4-methylbenzyl)oxy]-3-(thiophen-2-yl)quinolin-2(1H)-one;
4-(piperidin-3-ylmethoxy)-3-(thiophen-2-yl)quinolin-2(1H)-one;
4-(2,2-dimethylpropoxy)-3-(thiophen-2-yl)quinolin-2(1H)-one;
6-bromo-3-phenyl-4-(pyridin-2-ylmethoxy)quinolin-2(1H)-one;
3-phenyl-4-[(E)-2-(pyridin-2-yl)ethenyl]quinolin-2(1H)-one;
4-(benzyloxy)-6-bromo-3-phenylquinolin-2(1H)-one;
6-(3-nitrophenyl)-4-(pyridin-2-ylmethoxy)-3-(thiophen-2-yl)quinolin-2(1H)-one;
4-(pyridin-2-ylmethoxy)-6-(pyrimidin-5-yl)-3-(thiophen-2-yl)quinolin-2(1H)-one;
4-[2-oxo-4-(pyridin-2-ylmethoxy)-3-(thiophen-2-yl)-1,2-dihydroquinolin-6-yl]benzonitrile;
6-(pyridin-4-yl)-4-(pyridin-2-ylmethoxy)-3-(thiophen-2-yl)quinolin-2(1H)-one;
6-ethenyl-4-(pyridin-2-ylmethoxy)-3-(thiophen-2-yl)quinolin-2(1H)-one;
6-(1H-pyrazol-4-yl)-4-(pyridin-2-ylmethoxy)-3-(thiophen-2-yl)quinolin-2(1H)-one;
6-bromo-4-[(E)-2-(pyridin-2-yl)ethenyl]-3-(thiophen-2-yl)quinolin-2(1H)-one;
6-bromo-4-(cyclohexylmethoxy)-3-(thiophen-2-yl)quinolin-2(1H)-one;
6-bromo-4-(tetrahydro-2H-pyran-4-ylmethoxy)-3-(thiophen-2-yl)quinolin-2(1H)-one;
4-(cyclohexylmethoxy)-6-(3-hydroxy-3-methylbut-1-yn-1-yl)-3-(thiophen-2-yl)quinolin-2(1H)-one;
4-[(E)-2-(pyridin-2-yl)ethenyl]-3-(thiophen-2-yl)quinolin-2(1H)-one;
4-[2-(pyridin-2-yl)ethyl]-3-(thiophen-2-yl)quinolin-2(1H)-one;
6-(3-hydroxy-3-methylbut-1-yn-1-yl)-4-(tetrahydro-2H-pyran-4-ylmethoxy)-3-(thiophen-2-yl)quinolin-2(1H)-one;
4-(3-ethylphenyl)-3-(thiophen-2-yl)quinolin-2(1H)-one;
4-[3-(pyridin-3-yl)phenyl]-3-(thiophen-2-yl)quinolin-2(1H)-one;
4-[3-(pyridin-2-yl)phenyl]-3-(thiophen-2-yl)quinolin-2(1H)-one;
4-[3-(3-hydroxy-3-methylbut-1-yn-1-yl)phenyl]-3-(thiophen-2-yl)quinolin-2(1H)-one;
4-[3-(3,3-dimethylbut-1-yn-1-yl)phenyl]-3-(thiophen-2-yl)quinolin-2(1H)-one;
6,7-dimethoxy-4-[3-(pyridin-2-yl)phenyl]-3-(thiophen-2-yl)quinolin-2(1H)-one;
6,7-dimethoxy-4-[3-(phenylethynyl)phenyl]-3-(thiophen-2-yl)quinolin-2(1H)-one;
6,7-dimethoxy-4-[3-(pyridin-2-ylethynyl)phenyl]-3-(thiophen-2-yl)quinolin-2(1H)-one;
4-[3-(3,3-dimethylbut-1-yn-1-yl)phenyl]-6,7-dimethoxy-3-(thiophen-2-yl)quinolin-2(1H)-one;
6,7-dimethoxy-4-[3-(pyridin-4-yl)phenyl]-3-(thiophen-2-yl)quinolin-2(1H)-one;
4-(biphenyl-3-yl)-3-(thiophen-2-yl)quinolin-2(1H)-one;
4-(3-cyclopropylphenyl)-6,7-dimethoxy-3-(thiophen-2-yl)quinolin-2(1H)-one;
4-[3-(phenylethynyl)phenyl]-3-(thiophen-2-yl)quinolin-2(1H)-one;
6,7-dimethoxy-4-[3-(pyridin-3-yl)phenyl]-3-(thiophen-2-yl)quinolin-2(1H)-one;
6,7-dimethoxy-4-{3-[(E)-2-(pyridin-2-yl)ethenyl]phenyl}-3-(thiophen-2-yl)quinolin-2(1H)-one;
4-(3-ethylphenyl)-6,7-dimethoxy-3-(thiophen-2-yl)quinolin-2(1H)-one;
6,7-dimethoxy-4-[3-(propan-2-yl)phenyl]-3-(thiophen-2-yl)quinolin-2(1H)-one;
6,7-dimethoxy-4-[3-(2-methylpropyl)phenyl]-3-(thiophen-2-yl)quinolin-2(1H)-one;
4-[3-(pyridin-3-ylethynyl)phenyl]-3-(thiophen-2-yl)quinolin-2(1H)-one;
6,7-dimethoxy-4-[3-(pyridin-4-ylethynyl)phenyl]-3-(thiophen-2-yl)quinolin-2(1H)-one;
4-[3-(3-hydroxy-3-methylbut-1-yn-1-yl)phenyl]-6,7-dimethoxy-3-(thiophen-2-yl)quinolin-2(1H)-one;
6,7-dimethoxy-4-{3-[(E)-2-phenylethenyl]phenyl}-3-(thiophen-2-yl)quinolin-2(1H)-one;
4-(biphenyl-3-yl)-6,7-dimethoxy-3-(thiophen-2-yl)quinolin-2(1H)-one;
6,7-dimethoxy-4-{3-[(E)-2-(pyridin-3-yl)ethenyl]phenyl}-3-(thiophen-2-yl)quinolin-2(1H)-one;
6,7-dimethoxy-4-{3-[(E)-2-(pyridin-4-yl)ethenyl]phenyl}-3-(thiophen-2-yl)quinolin-2(1H)-one;
4-(3-cyclopentylphenyl)-3-(thiophen-2-yl)quinolin-2(1H)-one;
4-[3-(propan-2-yl)phenyl]-3-(thiophen-2-yl)quinolin-2(1H)-one;
4-(3-cyclopentylphenyl)-6,7-dimethoxy-3-(thiophen-2-yl)quinolin-2(1H)-one;
4-[3-(pyridin-2-ylethynyl)phenyl]-3-(thiophen-2-yl)quinolin-2(1H)-one;
4-[3-(pyridin-3-yl)phenyl]-3-(thiophen-2-yl)quinolin-2(1H)-one;
4-[3-(pyridin-4-yl)phenyl]-3-(thiophen-2-yl)quinolin-2(1H)-one;
4-(3-cyclopropylphenyl)-3-(thiophen-2-yl)quinolin-2(1H)-one;
4-{3-[(E)-2-phenylethenyl]phenyl}-3-(thiophen-2-yl)quinolin-2(1H)-one;

4-{3-[(E)-2-(pyridin-2-yl)ethenyl]phenyl}-3-(thiophen-2-yl)quinolin-2(1H)-one;

4-{3-[(E)-2-(pyridin-3-yl)ethenyl]phenyl}-3-(thiophen-2-yl)quinolin-2(1H)-one;

4-{3-[(E)-2-(pyridin-4-yl)ethenyl]phenyl}-3-(thiophen-2-yl)quinolin-2(1H)-one or a pharmaceutically acceptable salt thereof.

12. A pharmaceutical composition which comprises a pharmaceutically acceptable carrier and a compound of claim 1 or a pharmaceutically acceptable salt thereof.

13. A compound of claim 1 or a pharmaceutically acceptable salt thereof for use in medicine.

14. A method for treating a neurological or psychiatric disorder associated with PDE2 dysfunction in a mammalian patient in need thereof which comprises administering to the patient a therapeutically effective amount of a compound of claim 1 or a pharmaceutically acceptable salt thereof.

15. A method for treating a neurological or psychiatric disorder associated with striatal hypofunction or basal ganglia dysfunction in a mammalian patient in need thereof which comprises administering to the patient a therapeutically effective amount of a compound of claim 1 or a pharmaceutically acceptable salt thereof.

16. A method for treating schizophrenia in a mammalian patient in need thereof which comprises administering to the patient a therapeutically effective amount of a compound of claim 1 or a pharmaceutically acceptable salt thereof.

17. A method for treating bipolar disorder in a mammalian patient in need thereof which comprises administering to the patient a therapeutically effective amount of a compound of claim 1 or a pharmaceutically acceptable salt thereof.

18. A method for treating Huntington's disease in a mammalian patient in need thereof which comprises administering to the patient a therapeutically effective amount of a compound of claim 1 or a pharmaceutically acceptable salt thereof.

19. A method for enhancing cognition in a mammalian patient in need thereof which comprises administering to the patient a therapeutically effective amount of a compound of claim 1 or a pharmaceutically acceptable salt thereof.

20. A method for treating anxiety in a mammalian patient in need thereof which comprises administering to the patient a therapeutically effective amount of a compound of claim 1 or a pharmaceutically acceptable salt thereof.

* * * * *